US011142778B2

(12) United States Patent
Shirai et al.

(10) Patent No.: US 11,142,778 B2
(45) Date of Patent: Oct. 12, 2021

(54) DECARBOXYLASE AND METHOD FOR PRODUCING UNSATURATED HYDROCARBON COMPOUND USING SAME

(71) Applicant: RIKEN, Wako (JP)

(72) Inventors: Tomokazu Shirai, Wako (JP); Yutaro Mori, Wako (JP)

(73) Assignee: RIKEN, Wako (JP)

( * ) Notice: Subject to any disclaimer, the term of this patent is extended or adjusted under 35 U.S.C. 154(b) by 0 days.

(21) Appl. No.: 16/633,431

(22) PCT Filed: Jul. 24, 2018

(86) PCT No.: PCT/JP2018/027729
§ 371 (c)(1),
(2) Date: Jan. 23, 2020

(87) PCT Pub. No.: WO2019/022083
PCT Pub. Date: Jan. 31, 2019

(65) Prior Publication Data
US 2021/0130854 A1 May 6, 2021

(30) Foreign Application Priority Data
Jul. 24, 2017 (JP) .............................. JP2017-142930

(51) Int. Cl.
C12N 9/88 (2006.01)
C12P 7/40 (2006.01)
C12P 5/02 (2006.01)
C12P 7/42 (2006.01)

(52) U.S. Cl.
CPC ................. C12P 7/40 (2013.01); C12N 9/88 (2013.01); C12P 5/026 (2013.01); C12P 7/42 (2013.01); C12Y 401/01 (2013.01)

(58) Field of Classification Search
CPC ............... C12P 7/42; C12P 5/026; C12N 9/88
See application file for complete search history.

(56) References Cited

U.S. PATENT DOCUMENTS

| 2012/0225466 A1 | 9/2012 | Burk et al. |
| 2013/0330795 A1 | 12/2013 | Leys et al. |
| 2014/0141482 A1 | 5/2014 | Pearlman et al. |

FOREIGN PATENT DOCUMENTS

| JP | 2014-030376 A | 2/2014 |
| JP | 2015-228804 A | 12/2015 |
| WO | 2012/106516 A1 | 8/2012 |
| WO | 2012/174439 A2 | 12/2012 |
| WO | 2013/082264 A1 | 6/2013 |
| WO | 2013/192543 A2 | 12/2013 |
| WO | 2014/202838 A1 | 12/2014 |
| WO | 2017/033965 A1 | 3/2017 |

OTHER PUBLICATIONS

Accession No. CEN61045, Putative Ferulic acid decarboxylase 1 [Aspergillus calidoustus], Jan. 4, 2016. (Year: 2016).*
"Putative Ferulic acid decarboxylase 1 [Aspergillus calidoustus]", GenBank: CEN61045.1, 2016, available at https://www.ncbi.nlm.nih.gov/protein/CEN61045.
"5-Carboxyvanillate decarboxylase [Sphingomonas paucimobilis]", DB;GenBank, 2002, available at https://www.ncbi.nlm.nih.gov/protein/BAB86295.
"UbiD family decarboxylase [Catenulispora acidiphila DSM 44928]", DB;Bank, 2018, available at https://www.ncbi.nlm.nih.gov/protein/ACU72559.
Karl A. Payne et al., "New cofactor supports α,β-unsaturated acid decarboxylation via 1,3-dipolar cycloaddition", Nature, 2015, pp. 497-501, vol. 522.
Heike E. Weber et al., "Requirement of a Functional Flavin Mononucleotide Prenyltransferase for the Activity of a Bacterial Decarboxylase in a Heterologous Muconic Acid Pathway in *Saccharomyces cerevisiae*", Appl. Environ. Microbiol. May 2017, vol. 83, No. 10, e03472-16.
International Search Report for PCT/JP2018/027729, dated Oct. 30, 2018.
Communication, dated Mar. 1, 2021, issued by the European Patent Office in counterpart European application No. 18837722.0.

* cited by examiner

Primary Examiner — Tekchand Saidha
(74) Attorney, Agent, or Firm — Sughrue Mion, PLLC

(57) ABSTRACT

With the aim of providing a method allowing production of an unsaturated hydrocarbon compound such as butadiene with high productivity and an enzyme used in the method, the present inventors introduced mutations involving amino acid replacement into various positions of a ferulic acid decarboxylase, and prepared multiple modified forms of the enzyme. Then, the present inventors evaluated those modified forms in terms of the catalytic activity for the production of butadiene, and found as a result that the catalytic activity was improved in the case where, for example, the amino acid at position 395 was glutamine, histidine, asparagine, leucine, isoleucine, methionine, lysine, serine, arginine, tyrosine, or phenylalanine.

4 Claims, 7 Drawing Sheets
Specification includes a Sequence Listing.

Fig. 3

| | Unipot_ID | Derived from | (Number of amino acid residues that match the sequence of A. niger-derived FDC) / (Number of amino acid residues of A. niger-derived FDC) [%] | (Number of amino acid residues that match the sequence of A. niger-derived FDC) / (Number of amino acid residues of X-derived FDC) [%] |
|---|---|---|---|---|
| 1 | A0A1L9U2T1 | Aspergillus brasiliensis CBS 101740 | 98.4 | 98.4 |
| 2 | G7XVA2 | Aspergillus kawachii | 97.8 | 97.8 |
| 3 | A0A1L9N1V5 | Aspergillus tubingensis CBS 134.48 | 97.8 | 97.8 |
| 4 | A0A124BYZ7 | Aspergillus niger | 97.6 | 97.6 |
| 5 | A0A146FW50 | Aspergillus luchuensis | 97.6 | 97.6 |
| 6 | A0A1Q5UJS2 | Penicillium subrubescens | 84.4 | 84.4 |
| 7 | A0A1L9R520 | Aspergillus wentii DTO 134E9 | 84.2 | 84.4 |
| 8 | A0A0A2J5F4 | Penicillium expansum | 84 | 84 |
| 9 | K9FGD2 | Penicillium digitatum | 83.8 | 84 |
| 10 | A0A017SAW2 | Aspergillus ruber CBS 135680 | 83.8 | 83.8 |
| 11 | A0A0G4P429 | Penicillium camemberti | 83.6 | 83.6 |
| 12 | A0A161XU08 | Penicillium chrysogenum | 83.2 | 83.2 |
| 13 | A0A0M9WF89 | Penicillium nordicum | 83 | 83 |
| 14 | A0A1L9VVP0 | Aspergillus glaucus CBS 516.65 | 82.8 | 82.8 |
| 15 | A0A1E3B147 | Aspergillus cristatus | 82.2 | 82.2 |
| 16 | A0A135LJP5 | Penicillium patulum | 82 | 82 |
| 17 | A0A0F7U117 | Penicillium brasilianum | 82 | 81.5 |
| 18 | A0A009NTQ8 | Metarhizium anisopliae BRIP 53293 | 81.8 | 81.8 |
| 19 | A0A0B4GIB4 | Metarhizium guizhouense ARSEF 977 | 81.8 | 81.8 |
| 20 | A0A014P6U4 | Metarhizium robertsii | 81.8 | 80.5 |
| 21 | W6QKP7 | Penicillium roqueforti (strain FM164) | 81.4 | 81.7 |
| 22 | A0A1F5L787 | Penicillium arizonense | 80.8 | 80.8 |
| 23 | A0A0K8LG51 | Aspergillus udagawae | 79.4 | 78.6 |
| 24 | A0A0F0IHE5 | Aspergillus parasiticus | 79.2 | 78.7 |
| 25 | A0A1L9WTP9 | Aspergillus aculeatus ATCC 16872 | 79 | 78.5 |
| 26 | A0A1F8AA53 | Aspergillus bombycis | 79 | 78.5 |
| 27 | Q2UP67 | Aspergillus oryzae | 78.8 | 78.3 |
| 28 | A1DCG7 | Neosartorya fischeri | 78.8 | 78 |
| 29 | A0A0S7DJV6 | Aspergillus lentulus | 78.8 | 78 |
| 30 | A0A0L1J9Y6 | Aspergillus nomius NRRL 13137 | 78.2 | 77.7 |
| 31 | A0A0F8UFA2 | Aspergillus rambellii | 77.4 | 77.9 |
| 32 | A0A0U5FRV8 | Aspergillus calidoustus | 77 | 73.6 |
| 33 | A0A1L9PYZ1 | Aspergillus versicolor CBS 583.65 | 77 | 77 |
| 34 | A0A1L9T8N0 | Aspergillus sydowii CBS 593.65 | 76 | 75.7 |
| 35 | A0A060T4A6 | Blastobotrys adeninivorans | 75.8 | 76.3 |
| 36 | R1EM06 | Botryosphaeria parva | 74.4 | 75.2 |
| 37 | K2RUE8 | Macrophomina phaseolina | 72.8 | 73.7 |

Fig. 4

| | Unipot_ID | Derived from | (Number of amino acid residues that match the sequence of A. niger-derived FDC) / (Number of amino acid residues of A. niger-derived FDC) [%] | (Number of amino acid residues that match the sequence of A. niger-derived FDC) / (Number of amino acid residues of X-derived FDC) [%] |
|---|---|---|---|---|
| 38 | W9YNA8 | Capronia coronata CBS 617.96 | 72.6 | 72.9 |
| 39 | A0A1L7WN14 | Phialocephala subalpina | 72.2 | 68.4 |
| 40 | G9MXT8 | Hypocrea virens | 72 | 70.5 |
| 41 | A0A0D0U0M0 | Cryptococcus gattii VGII Ru05 | 71.8 | 71.7 |
| 42 | A0A095C6V3 | Cryptococcus gattii serotype B | 71.6 | 71.5 |
| 43 | A0A0G0A274 | Trichoderma harzianum | 71.6 | 70.1 |
| 44 | M3DF95 | Sphaerulina musiva (strain SO2202) | 71.2 | 70.1 |
| 45 | J9VVU7 | Cryptococcus neoformans var. grubii serotype A | 71 | 66.7 |
| 46 | A0A100IU15 | Aspergillus niger | 70.8 | 68.5 |
| 47 | A0A094IED9 | Pseudogymnoascus sp. VKM F-4520 (FW-2644) | 70.6 | 59.9 |
| 48 | A0A0W7V9B7 | Trichoderma gamsii | 70.6 | 68.9 |
| 49 | A0A1L9N5Q2 | Aspergillus tubingensis CBS 134.48 | 70.6 | 71.6 |
| 50 | H3H3G9 | Phytophthora ramorum | 70.4 | 64.6 |
| 51 | G9NLP6 | Hypocrea atroviridis | 70.2 | 68.6 |
| 52 | M7THT1 | Botryotinia fuckeliana (strain BcDW1) | 69.8 | 68 |
| 53 | G2XWX0 | Botryotinia fuckeliana | 69.6 | 67.8 |
| 54 | A0A1L9WL61 | Aspergillus aculeatus ATCC 16872 | 69.6 | 70.4 |
| 55 | A0A1L7SUP6 | Fusarium mangiferae | 69.6 | 69.2 |
| 56 | N1RYW4 | Fusarium oxysporum f. sp. cubense (strain race 4) | 69.6 | 69.2 |
| 57 | F9FQB3 | Fusarium oxysporum | 69.6 | 68.8 |
| 58 | A0A0G2EQF2 | Phaeomoniella chlamydospora | 69.6 | 69.9 |
| 59 | W9HNN8 | Fusarium oxysporum FOSC 3-a | 69.4 | 69 |
| 60 | X0BC97 | Fusarium oxysporum f. sp. raphani 54005 | 69.4 | 69 |
| 61 | W9WWR1 | Cladophialophora psammophila CBS 110553 | 69.4 | 69 |
| 62 | A0A0D2DPQ1 | Phialophora americana | 69.4 | 69.5 |
| 63 | S0E299 | Gibberella fujikuroi | 69.4 | 69 |
| 64 | A0A0J0BVX6 | Gibberella fujikuroi | 69.2 | 68.8 |
| 65 | N4TMS4 | Fusarium oxysporum f. sp. cubense | 69.2 | 68.8 |
| 66 | W9JNI1 | Fusarium oxysporum Fo47 | 69.2 | 68.8 |
| 67 | A0A010QFR6 | Colletotrichum fioriniae PJ7 | 69 | 68.6 |
| 68 | A0A0D2YAR9 | Fusarium oxysporum f. sp. lycopersici | 69 | 68.6 |
| 69 | A0A0D2IKD5 | Cladophialophora bantiana CBS 173.52 | 69 | 68.6 |
| 70 | A0A0D2AQI6 | Cladophialophora immunda | 68.8 | 68.1 |
| 71 | X0A148 | Fusarium oxysporum f. sp. melonis 26406 | 68.8 | 68.4 |
| 72 | A0A135TY05 | Colletotrichum nymphaeae SA-01 | 68.8 | 68.1 |
| 73 | L2G6I9 | Colletotrichum gloeosporioides | 68.6 | 67.8 |
| 74 | A0A1L7VCR5 | Fusarium proliferatum ET1 | 68.6 | 68.2 |

Fig. 5

| # | Unipot_ID | Derived from | (Number of amino acid residues that match the sequence of A. niger-derived FBC) / (Number of amino acid residues of A. niger-derived FBC) (%) | (Number of amino acid residues that match the sequence of A. niger-derived FBC) / (Number of amino acid residues of X-derived FBC) (%) |
|---|---|---|---|---|
| 75 | W3XQA0 | Pestalotiopsis fici W106-1 | 68.4 | 68.3 |
| 76 | A0A135URQ4 | Colletotrichum salicis | 68.4 | 67.7 |
| 77 | A0A164BB14 | Colletotrichum orchidophilum | 68.4 | 66.7 |
| 78 | A0A1C1X2A9 | Diaporthe helianthi | 68.4 | 67.6 |
| 79 | N7MPN7 | Gibberella moniliformis | 68.2 | 67.8 |
| 80 | T0K816 | Colletotrichum gloeosporioides | 68 | 67.2 |
| 81 | A0A135RR59 | Colletotrichum simmondsii | 67.6 | 66.9 |
| 82 | A0A194VZG5 | Valsa mali var. pyri | 67.6 | 67.7 |
| 83 | A0A194VPQ6 | Valsa mali | 67.4 | 67.5 |
| 84 | W9NGN5 | Fusarium oxysporum f. sp. pisi HDV247 | 67.4 | 65.2 |
| 85 | E6RA84 | B (strain NN276 / ATCC MYA-4071) | 67.2 | 64.2 |
| 86 | A0A067K683 | Bionectria ochroleuca | 67.2 | 67.7 |
| 87 | A0A0D0YJ00 | Cryptococcus gattii EJB2 | 67 | 64.1 |
| 88 | A0A166N1L4 | Colletotrichum tofieldiae | 66.8 | 66 |
| 89 | A0A1J7J343 | Coniochaeta ligniaria NRRL 30616 | 66.8 | 66.4 |
| 90 | A0A0N8H5Z4 | Neonectria ditissima | 66.8 | 65.9 |
| 91 | S3D5R7 | Ophiostoma piceae | 66.8 | 66.8 |
| 92 | W9JP63 | Fusarium oxysporum Fo47 | 66.6 | 66.2 |
| 93 | W9ZFW9 | Fusarium oxysporum f. sp. melonis 26406 | 66.6 | 66.2 |
| 94 | F0XL98 | Grosmannia clavigera | 66.4 | 66.4 |
| 95 | W9HU82 | Fusarium oxysporum FOSC 3-a | 66.4 | 66 |
| 96 | H1VUR4 | Colletotrichum higginsianum (strain IMI 349063) | 66 | 65.2 |
| 97 | A0A0F9Z7X1 | Trichoderma harzianum | 64.8 | 64.9 |
| 98 | A0A0D0VV15 | Cryptococcus gattii CA1280 | 64 | 73.6 |
| 99 | A0A0D0X028 | Cryptococcus gattii VGIV IND107 | 64 | 73.6 |
| 100 | E6R9Z1 | Cryptococcus gattii serotype B | 63.6 | 73.1 |
| 101 | F0XKQ3 | Grosmannia clavigera | 62.8 | 65.1 |
| 102 | A0A0F4ZKG8 | Thielaviopsis punctulata | 62.2 | 62.3 |
| 103 | G4YRJ8 | Phytophthora sojae | 61 | 65.2 |
| 104 | C7Z1A7 | Nectria haematococca | 60.8 | 64.1 |
| 105 | A0A0F8U179 | Aspergillus ochraceoroseus | 60.6 | 76.7 |
| 106 | C7ZCQ9 | Nectria haematococca | 60.4 | 61.8 |
| 107 | T2BN40 | Cryptococcus neoformans var. grubii serotype A | 59 | 66 |
| 108 | A0A0G2FUZ8 | Diplodia seriata | 57.6 | 67.3 |
| 109 | C5E5Q6 | Zygosaccharomyces rouxii | 46.4 | 45.4 |
| 110 | A0A0T1NB51 | Mycobacterium sp. Root135 | 35.2 | 34.6 |
| 111 | A0A0A0WBQ5 | Phomopsis liquidambaris | 25.4 | 70.6 |
| 112 | N1RLH9 | Fusarium oxysporum f. sp. cubense | 20 | 59.9 |

Fig. 6

| | Unipot_ID | Derived from | (Number of amino acid residues that match the sequence of A. niger-derived FDC) / (Number of amino acid residues of A. niger-derived FDC) [%] | (Number of amino acid residues that match the sequence of A. niger-derived FDC) / (Number of amino acid residues of X-derived FDC) [%] |
|---|---|---|---|---|
| 1 | A0A0U5GN72 | Aspergillus calidoustus | 56.4 | 56.2 |
| 2 | A0A0F7TN83 | Penicillium brasilianum | 55.8 | 55.6 |
| 3 | A0A161VUU1 | Colletotrichum tofieldiae | 55.8 | 54.6 |
| 4 | A0A0K8L8H7 | Aspergillus udagawae | 55.8 | 55.6 |
| 5 | A0A178B9N2 | Stagonospora sp. SRC11sM3a | 55.4 | 52.5 |
| 6 | A0A1Q8S4B3 | Colletotrichum chlorophyti | 55.4 | 53.9 |
| 7 | A0A0J9UT52 | Fusarium oxysporum f. sp. lycopersici | 54.6 | 52 |
| 8 | W9IBB4 | Fusarium oxysporum FOSC 3-a | 54.6 | 52 |
| 9 | A0A0I9YJH8 | Gibberella fujikuroi | 54.4 | 51.8 |
| 10 | A0A178DVY8 | Pyrenochaeta sp. DS3sAY3a | 54.4 | 54.1 |
| 11 | W9NMZ4 | Fusarium oxysporum f. sp. pisi HDV247 | 54.4 | 51.8 |
| 12 | A0A1L7VV91 | Fusarium proliferatum ET1 | 54.2 | 51.6 |
| 13 | W7LPC4 | Gibberella moniliformis | 54.2 | 51.5 |
| 14 | X0ISV7 | Fusarium oxysporum f. sp. cubense tropical race 4 54006 | 54.2 | 51.6 |
| 15 | W9K353 | Fusarium oxysporum Fo47 | 54.2 | 51.6 |
| 16 | X0C9L0 | Fusarium oxysporum f. sp. raphani 54005 | 54.2 | 51.3 |
| 17 | S0E5U5 | Gibberella fujikuroi | 54.2 | 51.6 |
| 18 | X0MWB8 | Fusarium oxysporum f. sp. vasinfectum 25433 | 54 | 51.4 |
| 19 | X0HZI4 | Fusarium oxysporum f. sp. conglutinans race 2 54008 | 53.2 | 53.3 |
| 20 | X0BC06 | Fusarium oxysporum f. sp. raphani 54005 | 53.2 | 53.3 |
| 21 | A0A0D2XL95 | Fusarium oxysporum f. sp. lycopersici | 46.8 | 43.7 |
| 22 | N4TWX3 | Fusarium oxysporum f. sp. cubense | 46.4 | 43.4 |
| 23 | A0A1A3FMK0 | Mycobacterium sp. 1245801.1 | 39.8 | 40.1 |

Fig. 7

| | Unipot_ID | Derived from | (Number of amino acid residues that match the sequence of A. niger-derived FDC) / (Number of amino acid residues of A. niger-derived FDC) [%] | (Number of amino acid residues that match the sequence of A. niger-derived FDC) / (Number of amino acid residues of X-derived FDC) [%] |
|---|---|---|---|---|
| 1 | Q8RJ47 | Sphingomonas paucimobilis | 12.2 | 18.3 |

Fig. 8

| | Unipot_ID | Derived from | (Number of amino acid residues that match the sequence of A. niger-derived FDC) / (Number of amino acid residues of A. niger-derived FDC) [%] | (Number of amino acid residues that match the sequence of A. niger-derived FDC) / (Number of amino acid residues of X-derived FDC) [%] |
|---|---|---|---|---|
| 1 | C7QBU0 | Catenulispora acidiphila | 39.2 | 39.4 |

DECARBOXYLASE AND METHOD FOR PRODUCING UNSATURATED HYDROCARBON COMPOUND USING SAME

CROSS REFERENCE TO RELATED APPLICATIONS

This application is a National Stage of International Application No. PCT/JP2018/027729, filed Jul. 24, 2018, claiming priority based on Japanese Patent Application No. 2017-142930 filed Jul. 24, 2017.

TECHNICAL FIELD

The present invention relates to a method for producing an unsaturated hydrocarbon compound using a ferulic acid decarboxylase, the decarboxylase having glutamine or the like at position 395 or other position. The present invention also relates to a method for producing an unsaturated hydrocarbon compound using a host cell introduced with a DNA encoding the decarboxylase or a vector inserted with the DNA. Further, the present invention relates as well to an agent for promoting the production of an unsaturated hydrocarbon compound, containing the decarboxylase, the DNA, or the vector.

The present invention also relates to a ferulic acid decarboxylase modified form in which position 395 or other position is modified to glutamine or the like, and a method for producing the same, and further relates to a DNA encoding the ferulic acid decarboxylase modified form, a vector inserted with the DNA, and a host cell introduced with the DNA or the vector.

BACKGROUND ART

It can be said that butadiene (1,3-butadiene) is an extremely important organic compound in the chemical industry because it is used as a raw material for various polymer compounds, including various synthetic rubbers (such as butadiene rubber, styrene-butadiene rubber, and acrylonitrile-butadiene rubber), and polymer resins (such as ABS resin and Nylon 66). In addition, these polymer compounds using butadiene as a raw material are widely used not only for industrial products such as automobile tires but also for daily necessities such as clothing. Therefore, the demand for butadiene is increasing year by year. Its annual demand is 13 million tons, and the market size has reached 15 billion dollars.

Conventionally, butadiene has been produced by purifying the C4 fraction produced as a byproduct mainly in the process of producing ethylene and propylene from petroleum. However, due to environmental problems including the depletion of fossil fuels such as petroleum and global warming due to greenhouse gas emissions, there is an increasing need to achieve sustainable butadiene production to meet the above-mentioned increasing demand for butadiene. As a countermeasure against these problems, development has been actively conducted of a method which uses an enzyme to produce butadiene from a biomass resource-derived material that is a renewable resource.

For example, PTL 1 discloses a method for producing butadiene by using xylose as a raw material and a microorganism having an enzyme activity capable of converting xylose into crotyl alcohol or the like. In addition, PTL 2 discloses a method for producing butadiene by using xylose as a raw material and a microorganism having an enzyme activity capable of converting xylose into 2,3-butanediol.

Although many attempts have been made to produce unsaturated hydrocarbon compounds such as butadiene using an enzyme as described above, they are insufficient in terms of productivity.

CITATION LIST

Patent Literature

[PTL 1] Japanese Unexamined Patent Application Publication No. 2014-30376
[PTL 2] Japanese Unexamined Patent Application Publication No. 2015-228804

Non Patent Literature

[NPL 1] Karl A. P. Payne et al., Nature, published on Jun. 25, 2015, Volume 522, Issue 7557, Pages 497 to 501

SUMMARY OF INVENTION

Technical Problem

The present invention has been made in view of the above-described problems of the related art, and an object thereof is to provide an enzyme allowing production of an unsaturated hydrocarbon compound such as butadiene with high productivity.

Solution to Problem

The present inventors have made earnest studies in order to achieve the above object, and as a result conceived applying the production of 4-vinyl guaiacol (4VG) by decarboxylation reaction of ferulic acid, which involves a ferulic acid decarboxylase (see NPL 1 and the following formula), to the production of an unsaturated hydrocarbon compound such as butadiene.

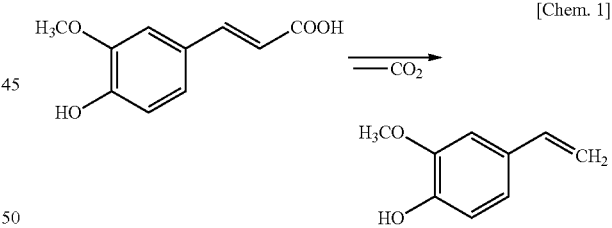

[Chem. 1]

Specifically, the present inventors conceived producing butadiene or the like through a decarboxylation reaction as represented by the following formula by introducing a mutation into an amino acid of a ferulic acid decarboxylase so as to allow the substrate specificity of the enzyme to change from originally being on ferulic acid to being on muconic acid or the like.

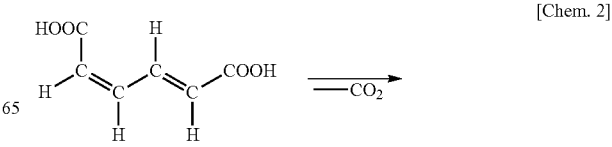

[Chem. 2]

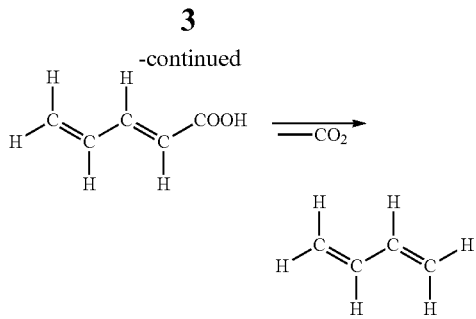

To this end, the present inventors introduced a mutation involving amino acid replacement into each of the 10 positions of an *Aspergillus niger*-derived ferulic acid decarboxylase (decarboxylase composed of the amino acid sequence set forth in SEQ ID NO: 2) to prepare 121 modified forms of ferulic acid decarboxylase. Then, the present inventors evaluated these modified forms in terms of catalytic activity for the production of butadiene using muconic acid as a substrate.

As a result, it was revealed that, at position 395 in the 10 positions introduced with mutations, when the threonine at the position was replaced with a different amino acid (glutamine, histidine, asparagine, lysine, serine, or arginine), the catalytic activity for the production of butadiene was almost improved (the catalytic activity was improved by at least about 3 times as compared with a wild type ferulic acid decarboxylase before mutagenesis).

Surprisingly, it was found that the catalytic activity for the production of butadiene was improved by nearly 50 times in the case of replacing position 395 with asparagine, nearly 70 times in the case of replacement with histidine, and 100 times or more in the case of replacement with glutamine as compared with a wild type ferulic acid decarboxylase.

Moreover, in each of the ferulic acid decarboxylases whose position 395 had been replaced with a different amino acid, an amino acid at different position was further replaced to prepare a modified form, which was also evaluated in terms of the above-described catalytic activity.

As a result, it was revealed that, in addition to the amino acid replacement at position 395 described above, replacement of position 394 with a different amino acid could further improve the catalytic activity for the production of 1,3-butadiene. Particularly surprisingly, it was found that, in the modified form whose position 395 had been replaced with histidine, the catalytic activity for the production of 1,3-butadiene was improved by 500 times or more in the case of replacing position 394 with serine, leucine, or methionine and 1000 times or more in the case of replacing the position with histidine as compared with wild type FDC.

In addition, the present inventors found that the catalytic activity of a ferulic acid decarboxylase for the production of 1,3-butadiene was improved as compared with the wild type also in the case of replacing only the tyrosine at position 394 with a different amino acid (phenylalanine, methionine, tryptophan, leucine, isoleucine, histidine, threonine, arginine, or asparagine) and in the case of replacing the phenylalanine at position 437 with tyrosine, in addition to the amino acid replacement at position 395 mentioned above. The above findings have led to the completion of the present invention.

Specifically, the present invention relates to a method for producing an unsaturated hydrocarbon compound using a ferulic acid decarboxylase, the decarboxylase having glutamine or the like at position 395 or other position. The present invention also relates to a method for producing an unsaturated hydrocarbon compound using a host cell introduced with a DNA encoding the decarboxylase or a vector inserted with the DNA. Further, the present invention relates as well to an agent for promoting the production of an unsaturated hydrocarbon compound containing the decarboxylase, the DNA, or the vector.

The present invention also relates to a ferulic acid decarboxylase modified form in which position 395 or other position is modified to glutamine or the like, and a method for producing the same, and further relates to a DNA encoding the ferulic acid decarboxylase modified form, a vector inserted with the DNA, and a host cell introduced with the DNA or the vector.

More specifically, the present invention provides the following.

<1> A method for producing an unsaturated hydrocarbon compound represented by the following formula (2) or a geometric isomer thereof, comprising: decarboxylating an unsaturated hydrocarbon dicarboxylic acid compound represented by the following formula (1) or a geometric isomer thereof in the presence of a ferulic acid decarboxylase in which an amino acid at position 395 of an amino acid sequence set forth in SEQ ID NO: 2 or corresponding to the position is glutamine, histidine, asparagine, leucine, isoleucine, methionine, lysine, serine, arginine, tyrosine, or phenylalanine

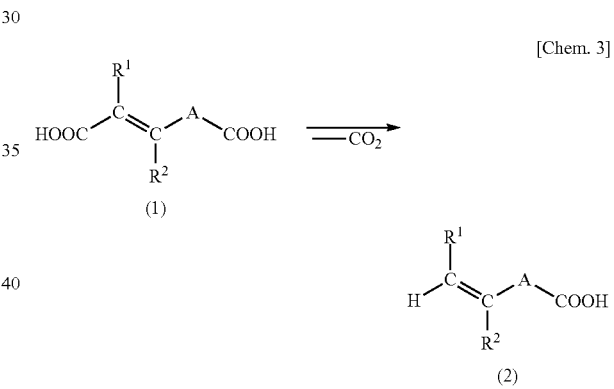

[In formulas (1) and (2), $R^1$ and $R^2$ each independently represent a hydrogen atom, a linear or branched alkyl group having 1 to 5 carbon atoms, a linear or branched alkoxy group having 1 to 5 carbon atoms, or hydroxyl group. "A" represents an optionally substituted linear hydrocarbon group having 0 to 5 carbon atoms, and may have a double bond formed between adjacent carbon atoms in the case of 2 to 5 carbon atoms.].

<2> A method for producing an unsaturated hydrocarbon compound represented by the following formula (5) or a geometric isomer thereof, comprising: decarboxylating an unsaturated hydrocarbon dicarboxylic acid compound represented by the following formula (3) or a geometric isomer thereof in the presence of a ferulic acid decarboxylase in which an amino acid at position 395 of an amino acid sequence set forth in SEQ ID NO: 2 or corresponding to the position is glutamine, histidine, asparagine, leucine, isoleucine, methionine, lysine, serine, arginine, tyrosine, or phenylalanine

[Chem. 4]

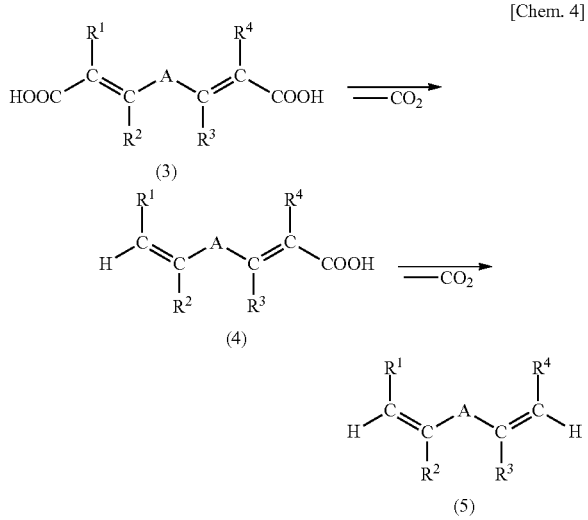

[In formulas (3) to (5), $R^1$, $R^2$, $R^3$, and $R^4$ each independently represent a hydrogen atom, a linear or branched alkyl group having 1 to 5 carbon atoms, a linear or branched alkoxy group having 1 to 5 carbon atoms, or hydroxyl group. "A" represents an optionally substituted linear hydrocarbon group having 0 to 5 carbon atoms, and may have a double bond formed between adjacent carbon atoms in the case of 2 to 5 carbon atoms.].

<3> A method for producing an unsaturated hydrocarbon compound, comprising: culturing a host cell introduced with a DNA or a vector containing the DNA, the DNA encoding a ferulic acid decarboxylase in which an amino acid at position 395 of an amino acid sequence set forth in SEQ ID NO: 2 or corresponding to the position is glutamine, histidine, asparagine, leucine, isoleucine, methionine, lysine, serine, arginine, tyrosine, or phenylalanine; and collecting an unsaturated hydrocarbon compound represented by the following formula (2) or (5) or a geometric isomer thereof produced in the host cell and/or a culture thereof.

[Chem. 5]

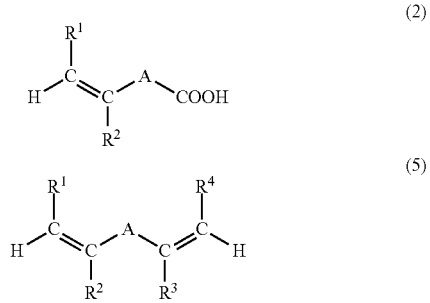

[In formulas (2) and (5), $R^1$, $R^2$, $R^3$, and $R^4$ each independently represent a hydrogen atom, a linear or branched alkyl group having 1 to 5 carbon atoms, a linear or branched alkoxy group having 1 to 5 carbon atoms, or hydroxyl group. "A" represents an optionally substituted linear hydrocarbon group having 0 to 5 carbon atoms, and may have a double bond formed between adjacent carbon atoms in the case of 2 to 5 carbon atoms.].

<4> The method for producing an unsaturated hydrocarbon compound according to any one of <1> to <3>, wherein the ferulic acid decarboxylase is a ferulic acid decarboxylase in which the amino acid at position 395 of the amino acid sequence set forth in SEQ ID NO: 2 or corresponding to the position is glutamine, and an amino acid at position 394 of the amino acid sequence set forth in SEQ ID NO: 2 or corresponding to the position is histidine, methionine, serine, or leucine.

<5> A ferulic acid decarboxylase comprising: an amino acid at position 395 of an amino acid sequence set forth in SEQ ID NO: 2 or corresponding to the position, the amino acid modified to glutamine, histidine, asparagine, leucine, isoleucine, methionine, lysine, serine, arginine, tyrosine, or phenylalanine, wherein the ferulic acid decarboxylase has catalytic activity for producing an unsaturated hydrocarbon compound represented by the following formula (2) or (5) or a geometric isomer thereof

[Chem. 6]

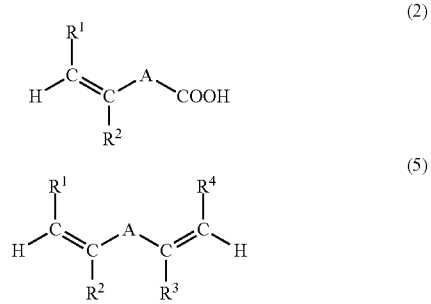

[In formulas (2) and (5), $R^1$, $R^2$, $R^3$, and $R^4$ each independently represent a hydrogen atom, a linear or branched alkyl group having 1 to 5 carbon atoms, a linear or branched alkoxy group having 1 to 5 carbon atoms, or hydroxyl group. "A" represents an optionally substituted linear hydrocarbon group having 0 to 5 carbon atoms, and may have a double bond formed between adjacent carbon atoms in the case of 2 to 5 carbon atoms.].

<6> The ferulic acid decarboxylase according to <5>, wherein the amino acid at position 395 of the amino acid sequence set forth in SEQ ID NO: 2 or corresponding to the position is modified to glutamine, and further, an amino acid at position 394 of the amino acid sequence set forth in SEQ ID NO: 2 or corresponding to the position is modified to histidine, methionine, serine, or leucine.

<7> A DNA encoding the ferulic acid decarboxylase according to <5> or <6>.

<8> A vector comprising the DNA according to <7>.

<9> A host cell introduced with the DNA according to <7> or the vector according to <8>.

<10> A method for producing a ferulic acid decarboxylase modified form, comprising: culturing the host cell according to <9>; and collecting a protein expressed in the host cell.

<11> A method for producing a ferulic acid decarboxylase with enhanced catalytic activity for producing an unsaturated hydrocarbon compound represented by the following formula (2) or (5) or a geometric isomer thereof, the method comprising: modifying, in a ferulic acid decarboxylase, an amino acid at position 395 of an amino acid sequence set forth in SEQ ID NO: 2 or corresponding to the position to glutamine, histidine, asparagine, leucine, isoleucine, methionine, lysine, serine, arginine, tyrosine, or phenylalanine.

[Chem. 7]

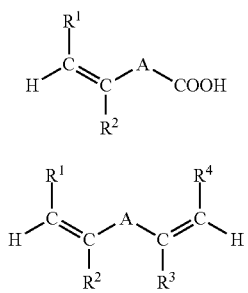

[In formulas (2) and (5), $R^1$, $R^2$, $R^3$, and $R^4$ each independently represent a hydrogen atom, a linear or branched alkyl group having 1 to 5 carbon atoms, a linear or branched alkoxy group having 1 to 5 carbon atoms, or hydroxyl group. "A" represents an optionally substituted linear hydrocarbon group having 0 to 5 carbon atoms, and may have a double bond formed between adjacent carbon atoms in the case of 2 to 5 carbon atoms.].

<12> The method according to <11>, wherein, in the ferulic acid decarboxylase, the amino acid at position 395 of the amino acid sequence set forth in SEQ ID NO: 2 or corresponding to the position is modified to glutamine, and an amino acid at position 394 of the amino acid sequence set forth in SEQ ID NO: 2 or corresponding to the position is modified to histidine, methionine, serine, or leucine.

<13> An agent for promoting production of an unsaturated hydrocarbon compound represented by the following formula (2) or a geometric isomer thereof by decarboxylating an unsaturated hydrocarbon dicarboxylic acid compound represented by the following formula (1) or a geometric isomer thereof, the agent comprising: a ferulic acid decarboxylase in which an amino acid at position 395 of an amino acid sequence set forth in SEQ ID NO: 2 or corresponding to the position is glutamine, histidine, asparagine, leucine, isoleucine, methionine, lysine, serine, arginine, tyrosine, or phenylalanine; a DNA encoding the ferulic acid decarboxylase; or a vector inserted with the DNA

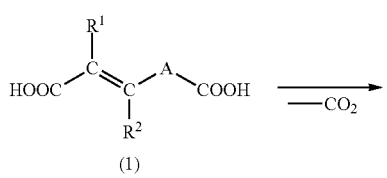

[In formulas (1) and (2), $R^1$ and $R^2$ each independently represent a hydrogen atom, a linear or branched alkyl group having 1 to 5 carbon atoms, a linear or branched alkoxy group having 1 to 5 carbon atoms, or hydroxyl group. "A" represents an optionally substituted linear hydrocarbon group having 0 to 5 carbon atoms, and may have a double bond formed between adjacent carbon atoms in the case of 2 to 5 carbon atoms.].

<14> An agent for promoting production of an unsaturated hydrocarbon compound represented by the following formula (5) or a geometric isomer thereof by decarboxylating an unsaturated hydrocarbon dicarboxylic acid compound represented by the following formula (3) or a geometric isomer thereof, the agent comprising: a ferulic acid decarboxylase in which an amino acid at position 395 of an amino acid sequence set forth in SEQ ID NO: 2 or corresponding to the position is glutamine, histidine, asparagine, leucine, isoleucine, methionine, lysine, serine, arginine, tyrosine, or phenylalanine; a DNA encoding the ferulic acid decarboxylase; or a vector inserted with the DNA

[Chem. 9]

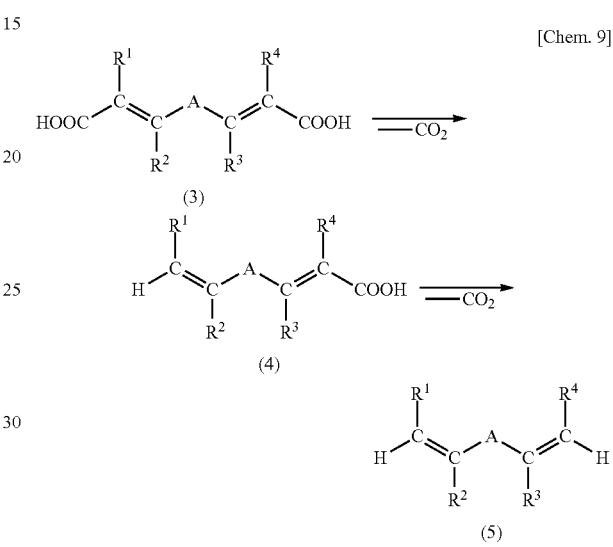

[In formulas (3) to (5), $R^1$, $R^2$, $R^3$, and $R^4$ each independently represent a hydrogen atom, a linear or branched alkyl group having 1 to 5 carbon atoms, a linear or branched alkoxy group having 1 to 5 carbon atoms, or hydroxyl group. "A" represents an optionally substituted linear hydrocarbon group having 0 to 5 carbon atoms, and may have a double bond formed between adjacent carbon atoms in the case of 2 to 5 carbon atoms.].

<15> The agent according to <13> or <14>, wherein the ferulic acid decarboxylase is a ferulic acid decarboxylase in which the amino acid at position 395 of the amino acid sequence set forth in SEQ ID NO: 2 or corresponding to the position is glutamine, and an amino acid at position 394 of the amino acid sequence set forth in SEQ ID NO: 2 or corresponding to the position is histidine, methionine, serine, or leucine.

<16> A method for producing the unsaturated hydrocarbon compound represented by the formula (2) or the geometric isomer thereof, comprising:
  decarboxylating the unsaturated hydrocarbon dicarboxylic acid compound represented by the formula (1) or the geometric isomer thereof in the presence of a ferulic acid decarboxylase, wherein
  the ferulic acid decarboxylase is at least one ferulic acid decarboxylase selected from the group consisting of the following (a) to (c)
(a) a ferulic acid decarboxylase in which an amino acid at position 395 of an amino acid sequence set forth in SEQ ID NO: 2 or corresponding to the position is glutamine, histidine, asparagine, leucine, isoleucine, methionine, lysine, serine, arginine, tyrosine, or phenylalanine, (b) a ferulic acid decarboxylase in which an amino acid at position 394 of the amino acid sequence set forth in SEQ ID NO: 2 or corresponding to the position is phenylalanine, methionine, tryptophan, leucine, isoleucine, histidine, threonine, arginine, or asparagine, and (c) a ferulic acid decarboxylase in which an amino acid at position 437 of the amino acid sequence set forth in SEQ ID NO: 2 or corresponding to the position is tyrosine, where in the formulas (1) and (2), $R^1$ and $R^2$ each independently represent a hydrogen atom, a linear or branched alkyl group having 1 to 5 carbon atoms, a linear or branched alkoxy group having 1 to 5 carbon atoms, or hydroxyl group. "A" represents an optionally substituted linear hydrocarbon group having 0 to 5 carbon atoms, and may have a double bond formed between adjacent carbon atoms in the case of 2 to 5 carbon atoms.

<17> A method for producing the unsaturated hydrocarbon compound represented by the formula (5) or the geometric isomer thereof, comprising:

decarboxylating the unsaturated hydrocarbon dicarboxylic acid compound represented by the formula (3) or the geometric isomer thereof in the presence of a ferulic acid decarboxylase, wherein the ferulic acid decarboxylase is at least one ferulic acid decarboxylase selected from the group consisting of the (a) to (c) according to <16>, where in the in the formulas (3) to (5), $R^1$, $R^2$, $R^3$, and $R^4$ each independently represent a hydrogen atom, a linear or branched alkyl group having 1 to 5 carbon atoms, a linear or branched alkoxy group having 1 to 5 carbon atoms, or hydroxyl group. "A" represents an optionally substituted linear hydrocarbon group having 0 to 5 carbon atoms, and may have a double bond formed between adjacent carbon atoms in the case of 2 to 5 carbon atoms.

<18> A method for producing an unsaturated hydrocarbon compound, comprising:

culturing a host cell introduced with a DNA encoding a ferulic acid decarboxylase or a vector containing the DNA; and collecting the unsaturated hydrocarbon compound represented by the formula (2) or (5) or the geometric isomer thereof produced in the host cell and/or a culture thereof, wherein the ferulic acid decarboxylase is at least one ferulic acid decarboxylase selected from the group consisting of the (a) to (c) according to <16>, where in the formulas (2) and (5), $R^1$, $R^2$, $R^3$, and $R^4$ each independently represent a hydrogen atom, a linear or branched alkyl group having 1 to 5 carbon atoms, a linear or branched alkoxy group having 1 to 5 carbon atoms, or hydroxyl group. "A" represents an optionally substituted linear hydrocarbon group having 0 to 5 carbon atoms, and may have a double bond formed between adjacent carbon atoms in the case of 2 to 5 carbon atoms.

<19> A ferulic acid decarboxylase having at least one modification selected from the group consisting of the following (d) to (f) introduced therein, and having catalytic activity for producing the unsaturated hydrocarbon compound represented by the formula (2) or (5) or the geometric isomer thereof (d) a ferulic acid decarboxylase such that an amino acid at position 395 of an amino acid sequence set forth in SEQ ID NO: 2 or corresponding to the position is modified to glutamine, histidine, asparagine, leucine, isoleucine, methionine, lysine, serine, arginine, tyrosine, or phenylalanine, (e) an amino acid at position 394 of the amino acid sequence set forth in SEQ ID NO: 2 or corresponding to the position is modified to phenylalanine, methionine, tryptophan, leucine, isoleucine, histidine, threonine, arginine, or asparagine, and (f) an amino acid at position 437 of the amino acid sequence set forth in SEQ ID NO: 2 or corresponding to the position is modified to tyrosine, where in the formulas (2) and (5), $R^1$, $R^2$, $R^3$, and $R^4$ each independently represent a hydrogen atom, a linear or branched alkyl group having 1 to 5 carbon atoms, a linear or branched alkoxy group having 1 to 5 carbon atoms, or hydroxyl group. "A" represents an optionally substituted linear hydrocarbon group having 0 to 5 carbon atoms, and may have a double bond formed between adjacent carbon atoms in the case of 2 to 5 carbon atoms.

<20> A DNA encoding the ferulic acid decarboxylase according to <19>.

<21> A vector comprising the DNA according to <20>.

<22> A host cell introduced with the DNA according to <20> or the vector according to <21>.

<23> A method for producing a ferulic acid decarboxylase modified form, comprising: culturing the host cell according to <22>; and collecting a protein expressed in the host cell.

<24> A method for producing a ferulic acid decarboxylase with enhanced catalytic activity for producing the unsaturated hydrocarbon compound represented by the formula (2) or (5) 16 or the geometric isomer thereof, the method comprising: introducing, in a ferulic acid decarboxylase, at least one modification selected from the group consisting of the (d) to (f) according to <19>.

Note that, in the formulas (2) and (5), $R^1$, $R^2$, $R^3$, and $R^4$ each independently represent a hydrogen atom, a linear or branched alkyl group having 1 to 5 carbon atoms, a linear or branched alkoxy group having 1 to 5 carbon atoms, or hydroxyl group. "A" represents an optionally substituted linear hydrocarbon group having 0 to 5 carbon atoms, and may have a double bond formed between adjacent carbon atoms in the case of 2 to 5 carbon atoms.

<25> An agent for promoting production of the unsaturated hydrocarbon compound represented by the formula (2) or the geometric isomer thereof by decarboxylating the unsaturated hydrocarbon dicarboxylic acid compound represented by the formula (1) or the geometric isomer thereof, the agent comprising: a ferulic acid decarboxylase; a DNA encoding the ferulic acid decarboxylase; or a vector inserted with the DNA, wherein the ferulic acid decarboxylase is at least one ferulic acid decarboxylase selected from the group consisting of the (a) to (c) according to <16>, where in the formulas (1) and (2), $R^1$ and $R^2$ each independently represent a hydrogen atom, a linear or branched alkyl group having 1 to 5 carbon atoms, a linear or branched alkoxy group having 1 to 5 carbon atoms, or hydroxyl group. "A" represents an optionally substituted linear hydrocarbon group having 0 to 5 carbon atoms, and may have a double bond formed between adjacent carbon atoms in the case of 2 to 5 carbon atoms.

<26> An agent for promoting production of the unsaturated hydrocarbon compound represented by the formula (5) or the geometric isomer thereof by decarboxylating the unsaturated hydrocarbon dicarboxylic acid compound represented by the formula (3) or the geometric isomer thereof, the agent comprising: a ferulic acid decarboxylase; a DNA encoding the ferulic acid decarboxylase; or a vector inserted with the DNA, wherein the ferulic acid decarboxylase is at least one ferulic acid decarboxylase selected from the group consisting of the (a) to (c) according to <16>, where in the formulas (3) to (5), $R^1$, $R^2$, $R^3$, and $R^4$ each independently represent a hydrogen atom, a linear or branched alkyl group having 1 to 5 carbon atoms, a linear or branched alkoxy group having 1 to 5 carbon atoms, or hydroxyl group. "A" represents an optionally substituted linear hydrocarbon group having 0 to 5 carbon atoms, and may have a double bond formed between adjacent carbon atoms in the case of 2 to 5 carbon atoms.

Advantageous Effects of Invention

The present invention makes it possible to provide an enzyme allowing production of an unsaturated hydrocarbon compound such as butadiene with high productivity, and a method for producing an unsaturated hydrocarbon compound using the enzyme.

BRIEF DESCRIPTION OF DRAWINGS

FIG. 3 depicts a table of ferulic acid decarboxylases.
FIG. 4 depicts a table of ferulic acid decarboxylases.
FIG. 5 depicts a table of ferulic acid decarboxylases.
FIG. 6 depicts a table of ferulic acid decarboxylases.
FIG. 7 depicts a table of ferulic acid decarboxylases.
FIG. 8 depicts a table of ferulic acid decarboxylases.

DESCRIPTION OF EMBODIMENTS

Figure 1:
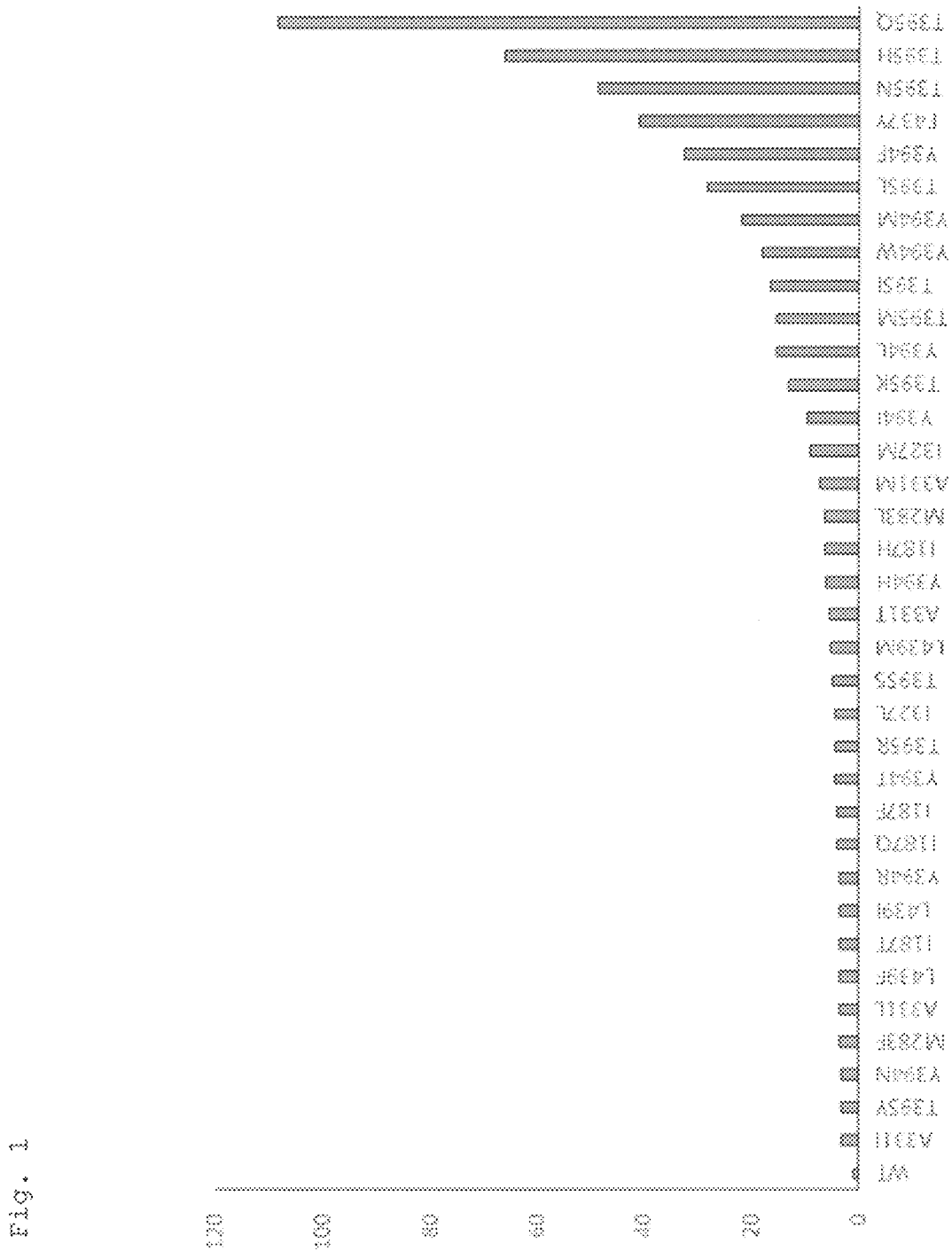
FIG. 1 is a graph illustrating the results of analyzing the catalytic activity for producing 1,3-butadiene using cis,cis-muconic acid as a substrate after expressing a modified form of a ferulic acid decarboxylase in *E. coli*, the modified form obtained by replacing each of the amino acids at 10 positions (leucine at position 185, isoleucine at position 187, methionine at position 283, threonine at position 323, isoleucine at position 327, alanine at position 331, tyrosine at position 394, threonine at position 395, phenylalanine at position 437, and leucine at position 439) with a different amino acid (arginine, lysine, histidine, serine, threonine, glutamine, asparagine, isoleucine, leucine, methionine, phenylalanine, tyrosine, or tryptophan). Note that, in the figure, the results are illustrated only for the modified forms whose catalytic activity was improved by 3 times or more as compared with a wild type ferulic acid decarboxylase. In the figure, the vertical axis represents the relative value calculated from the amount of 1,3-butadiene produced by each ferulic acid decarboxylase modified form where the wild type ferulic acid decarboxylase (WT) is a reference (1). In addition, in the figure, "A331I" and the like indicate the modified forms of a ferulic acid decarboxylase, the number represents the position (such as position 331) introduced with a mutation involving amino acid replacement in the enzyme, the alphabetical letter on the left side of the number represents the amino acid before replacement (such as A/alanine), and the alphabetical letter on the right side of the number represents the amino acid after replacement (such as I/isoleucine). The notation regarding the amino acid modified form is the same in FIG. 2 and Tables 8 to 12 unless otherwise specified.

<Method 1 for Producing Unsaturated Hydrocarbon Compound>

As presented in Examples to be described later, the present inventors have found that a ferulic acid decarboxylase in which the amino acid at position 395 is glutamine, histidine, asparagine, leucine, isoleucine, methionine, lysine, serine, arginine, tyrosine, or phenylalanine has a high catalytic activity for promoting the following reaction of producing an unsaturated hydrocarbon compound represented by the following formula (2) or (5) or a geometric isomer thereof (also referred to as the "catalytic activity for producing an unsaturated hydrocarbon compound").

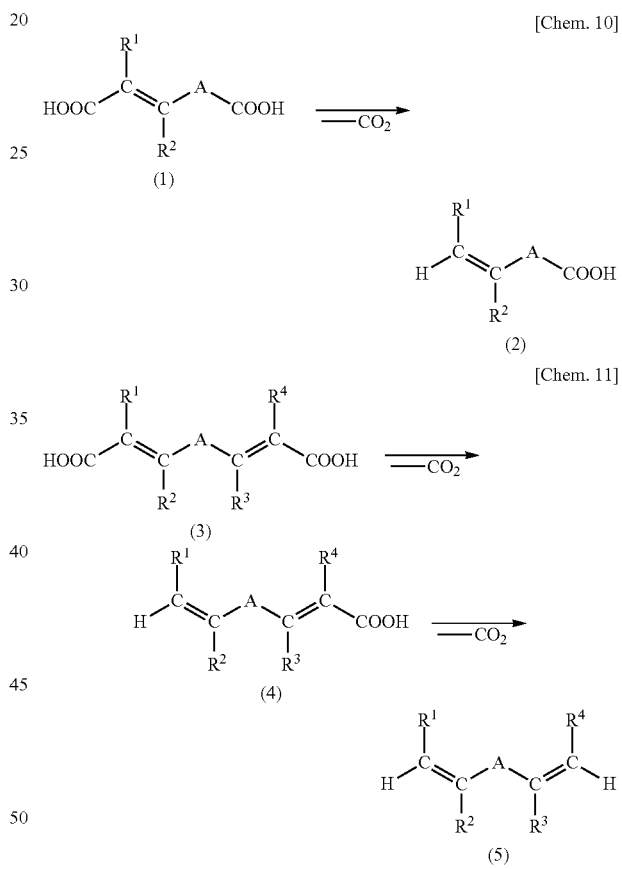

Therefore, the present invention provides a method for producing an unsaturated hydrocarbon compound represented by the following formula (2) or (5) or a geometric isomer thereof, comprising: decarboxylating an unsaturated hydrocarbon dicarboxylic acid compound represented by the following formula (1) or (3) or a geometric isomer thereof in the presence of a ferulic acid decarboxylase in which an amino acid at position 395 of an amino acid sequence set forth in SEQ ID NO: 2 or corresponding to the position is glutamine, histidine, asparagine, leucine, isoleucine, methionine, lysine, serine, arginine, tyrosine, or phenylalanine (hereinafter also referred to as the "decarboxylase according to the present invention." For the decarboxylase, see the later description).

In the present invention, "an unsaturated hydrocarbon compound or a geometric isomer thereof" produced by the reaction means a hydrocarbon compound having at least one carbon-carbon double bond as illustrated in the formulas (2) and (5), and may be one introduced with a linear or branched alkyl group having 1 to 5 carbon atoms, a linear or branched alkoxy group having 1 to 5 carbon atoms, or hydroxyl group. Examples of such compound include butadiene (1,3-butadiene), 2,4-pentadienoic acid, isocrotonic acid, 3-methylisocrotonic acid, 3-pentenoic acid, and 10-undecenoic acid.

In the present invention, "an unsaturated hydrocarbon dicarboxylic acid compound or a geometric isomer thereof" serving as a raw material for the production of the unsaturated hydrocarbon compound means a hydrocarbon compound having at least one carbon-carbon double bond and at least two carboxyl groups as illustrated in the formulas (1) and (3), and may be one introduced with a linear or branched alkyl group having 1 to 5 carbon atoms, a linear or branched alkoxy group having 1 to 5 carbon atoms, or hydroxyl group. Examples of such compound include cis,cis-muconic acid, cis,trans-muconic acid, trans, trans-muconic acid, glutaconic acid, 2-methylglutaconic acid, 3-methylglutaconic acid, and traumatic acid.

Such compounds represented by the formulas (1) and (3) and geometric isomers thereof can be purchased as commercially available products as presented in Examples to be described later. In addition, those skilled in the art can also synthesize with appropriate consideration of a known synthesis method (for example, the method described in Kiyoshi Kudo et al., the Journal of the Japan Petroleum Institute, published on Jul. 13, 1994, Volume 38, Issue 1, pages 48 to 51).

$R^1$ and $R^2$ in the compounds represented by the formulas (1) and (2) and geometric isomers thereof, or $R^1$, $R^2$, $R^3$, and $R^4$ in the compounds represented by the formulas (3) to (5) and geometric isomers thereof each independently represent a hydrogen atom, a linear or branched alkyl group having 1 to 5 carbon atoms, or a linear branched alkoxy group having 1 to 5 carbon atoms, or hydroxyl group.

Examples of the "linear or branched alkyl group having 1 to 5 carbon atoms" include a methyl group, an ethyl group, an n-propyl group, an i-propyl group, an n-butyl group, an i-butyl group, an s-butyl group, a t-butyl group, an n-pentyl group, and an i-pentyl group Examples of the "linear or branched alkoxy group having 1 to 5 carbon atoms" include a methoxy group, an ethoxy group, an n-propoxy group, an i-propoxy group, an n-butoxy group, an i-butoxy group, an s-butoxy group, a t-butoxy group, an n-pentyloxy group, an i-pentyloxy group, an n-pentyloxy group, and a 1,2-dimethyl-propoxy group.

In addition, "A" in the compounds represented by the formulas (1) to (5) and geometric isomers thereof represents an optionally substituted linear hydrocarbon group having 0 to 5 carbon atoms. Note that an "optionally substituted linear hydrocarbon group having 0 carbon atoms" means that, in the compounds represented by the formulas (1) to (5) and geometric isomers thereof, the carbon atoms bonded via "A" are directly bonded without the intermediary of "A".

Moreover, when the optionally substituted linear hydrocarbon group has 2 to 5 carbon atoms, at least one double bond may be formed between adjacent carbon atoms. In addition, examples of the substituents which the hydrocarbon group may have in "A" include a linear or branched alkyl group having 1 to 5 carbon atoms, a linear or branched alkoxy group having 1 to 5 carbon atoms, a hydroxyl group, a halogen atom (for example, fluorine, chlorine, bromine, or iodine), a nitro group, a cyano group, an amino group, a carboxyl group, and a formyl group.

It suffices that the condition of decarboxylating an unsaturated hydrocarbon dicarboxylic acid compound in the presence of the decarboxylase according to the present invention is a condition in which the decarboxylation is promoted and an unsaturated hydrocarbon compound is produced. Those skilled in the art can appropriately adjust and set the composition of the reaction liquid, the pH of the reaction liquid, the reaction temperature, the reaction time, and the like.

For example, the reaction liquid added with the decarboxylase according to the present invention and its substrate, the unsaturated hydrocarbon dicarboxylic acid compound, is not particularly limited as long as it does not interfere with the reaction, but preferably a buffer solution having a pH of 6 to 8 and more preferably a buffer solution having a pH of 6 to 7 and containing potassium chloride and sodium phosphate. Moreover, from the viewpoint of more easily promoting the reaction, it is preferable to contain prenylated flavin mononucleotide (prFMN) or an isomer thereof ($prFMN^{ketimine}$, $prFMN^{iminium}$, for these prFMN and isomers thereof, see NPL 1).

In addition, as the decarboxylase according to the present invention used in such a reaction, it is possible to use only one type of ferulic acid decarboxylase in which the amino acid at position 395 of the amino acid sequence set forth in SEQ ID NO: 2 or corresponding to the position is glutamine or the like, but it is also possible to use two or more types of the decarboxylase according to the present invention in combination. Moreover, as presented in Examples to be described later, from the viewpoint of more easily promoting the decarboxylation of the unsaturated hydrocarbon carboxylic acid compound, it is preferable to use in combination a ferulic acid decarboxylase in which the amino acid at position 395 of the amino acid sequence set forth in SEQ ID NO: 2 or corresponding to the position is threonine (for the "ferulic acid decarboxylase in which the amino acid at position 395 of the amino acid sequence set forth in SEQ ID NO: 2 or corresponding to the position is threonine," see FIGS. 3-5 to be described later).

In addition, the reaction temperature is not particularly limited either as long as the reaction is not hindered, but is usually 20 to 40° C. and preferably 25 to 37° C. Moreover, the reaction time is not particularly limited as long as it is a time for which the unsaturated hydrocarbon compound can be produced, but is usually 30 minutes to 7 days and preferably 12 hours to 2 days.

In addition, the unsaturated hydrocarbon compound produced under such conditions is generally easily vaporized, and thus can be collected by a known volatile gas recovery and purification method. Examples of such collection method include gas stripping, fractional distillation, adsorption, desorption, pervaporation, desorption of isoprene adsorbed on the solid phase from the solid phase by heat or vacuum, extraction with a solvent, and chromatography (for example, gas chromatography). In addition, when the olefin compound produced is a liquid, it can also be collected by appropriately using a known recovery and purification method (such as distillation and chromatography). Moreover, these methods may be carried out alone or may be carried out in multiple steps in appropriate combination.

<Method 2 for Producing Unsaturated Hydrocarbon Compound>

In addition, as presented in Examples to be described later, it is possible to produce an unsaturated hydrocarbon compound with high productivity by culturing a host cell transformed to express a ferulic acid decarboxylase, the decarboxylase having glutamine or the like at position 395.

Therefore, the present invention also provides a method for producing an unsaturated hydrocarbon compound, including culturing a host cell introduced with a DNA or a vector encoding the decarboxylase according to the present invention, and collecting the unsaturated hydrocarbon compound represented by the formula (2) or (5) or the geometric isomer thereof produced in the host cell and/or a culture thereof.

The "host cell introduced with a DNA or a vector encoding the decarboxylase according to the present invention" is as described later, but the decarboxylase according to the present invention expressed in such a host cell may be only one type of ferulic acid decarboxylase in which the amino acid at position 395 of the amino acid sequence set forth in SEQ ID NO: 2 or corresponding to the position is glutamine or the like, or may be two or more types of the decarboxylase according to the present invention. Moreover, as presented in Examples to be described later, from the viewpoint of more easily promoting the decarboxylation of the unsaturated hydrocarbon carboxylic acid compound, the host cell preferably also expresses a ferulic acid decarboxylase in which the amino acid at position 395 of the amino acid sequence set forth in SEQ ID NO: 2 or corresponding to the position is threonine.

In addition, the culture conditions for the cell are as described later, and the medium is preferably added with the unsaturated hydrocarbon dicarboxylic acid compound represented by the formula (1) or (3), which is a substrate of the decarboxylase according to the present invention, and a geometric isomer thereof. The culture temperature can be appropriately changed according to the type of the host cell to be used, but is usually 20 to 40° C. and preferably 25 to 37° C.

In addition, in the present invention, the "culture" is a medium containing proliferated host cells, secreted products of the host cells, metabolites of the host cells, and the like obtained by culturing the host cells in a medium, and includes dilutions and concentrates thereof.

The collection of an unsaturated hydrocarbon compound from such host cell and/or culture is not particularly limited either, and can be performed using the above-described known recovery and purification methods. In addition, the time period of collection is appropriately adjusted according to the type of the host cell to be used, and may be any time which can produce an unsaturated hydrocarbon compound, but is usually 30 minutes to 7 days and preferably 12 hours to 2 days.

<Decarboxylase According to Present Invention>

Next, description is provided for a decarboxylase used in e.g. the above-mentioned method for producing an unsaturated hydrocarbon compound of the present invention.

Usually, the "ferulic acid decarboxylase" is an enzyme registered as EC number: 4.1.1.102, and means an enzyme which catalyzes the following reaction of decarboxylating ferulic acid to produce 4-vinyl guaiacol (4VG).

[Chem. 12]

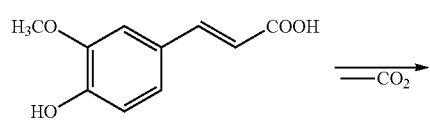

-continued

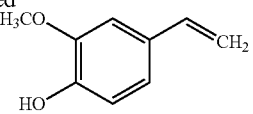

As mentioned above, the present inventors have found that a ferulic acid decarboxylase in which the amino acid at position 395 is glutamine or the like has a high catalytic activity for producing an unsaturated hydrocarbon compound.

Therefore, it suffices that the decarboxylase according to the present invention is a decarboxylase in which the amino acid at position 395 of the amino acid sequence set forth in SEQ ID NO: 2 or corresponding to the position is glutamine, histidine, asparagine, leucine, isoleucine, methionine, lysine, serine, arginine, tyrosine, or phenylalanine, and which has catalytic activity for producing an unsaturated hydrocarbon compound, and includes not only a ferulic acid decarboxylase in which the amino acid at the position is artificially modified to glutamine or the like (hereinafter also referred to as "ferulic acid decarboxylase modified form") as presented in Examples to be described later, but also a naturally occurring ferulic acid decarboxylase in which the amino acid at the position is glutamine or the like (hereinafter also referred to as the "ferulic acid decarboxylase homolog" or "ferulic acid decarboxylase natural mutant").

In the "ferulic acid decarboxylase modified form" of the present invention, the ferulic acid decarboxylase subjected to amino acid modification is not particularly limited, and ones derived from various organisms can be used. Examples thereof include a ferulic acid decarboxylase derived from *Aspergillus niger* (strain CBS513.88) (UNIPROT ID: A2QHE5, a ferulic acid decarboxylase composed of the amino acid sequence set forth in SEQ ID NO: 2) as well as a protein corresponding to "Ferulic acid decarboxylase" on UNIPROT, and specific examples include the ferulic acid decarboxylases described in FIGS. 3-8.

Note that FIGS. 3-5 present ferulic acid decarboxylases in each of which the amino acid at position 395 of the amino acid sequence set forth in SEQ ID NO: 2 or corresponding to the position is threonine, FIG. 6 presents ferulic acid decarboxylases in each of which the amino acid at position 395 of the amino acid sequence set forth in SEQ ID NO: 2 or corresponding to the position is glutamine, FIG. 7 presents a ferulic acid decarboxylase in which the amino acid at position 395 of the amino acid sequence set forth in SEQ ID NO: 2 or corresponding to the position is histidine, and FIG. 8 presents a ferulic acid decarboxylase in which the amino acid at position 395 of the amino acid sequence set forth in SEQ ID NO: 2 or corresponding to the position is asparagine. In addition, it should be understood that, in nature, a mutation in nucleotide sequence can cause a change in the amino acid sequence of a protein.

Among the ferulic acid decarboxylases described in FIGS. 3-8, the ferulic acid decarboxylase subjected to amino acid modification is preferably the ferulic acid decarboxylase derived from *Aspergillus niger*, and more preferably the protein composed of the amino acid sequence set forth in SEQ ID NO: 2.

In addition, examples of the "ferulic acid decarboxylase homolog" and "ferulic acid decarboxylase natural mutant" according to the present invention include the ferulic acid decarboxylases described in FIGS. 6-8, in which the position is glutamine, histidine, or arginine.

In the "decarboxylase according to the present invention," the amino acid at position 395 of the amino acid sequence set forth in SEQ ID NO: 2 or corresponding to the position may be glutamine, histidine, asparagine, leucine, isoleucine, methionine, lysine, serine, arginine, tyrosine, or phenylalanine, but is preferably glutamine, histidine, asparagine, leucine, isoleucine, methionine, or lysine, more preferably glutamine, histidine, or asparagine, further preferably glutamine or histidine, and particularly preferably glutamine from the viewpoint of a higher catalytic activity for producing an unsaturated hydrocarbon compound.

Moreover, in addition to the above-mentioned position 395, the further amino acid at position 394 of the amino acid sequence set forth in SEQ ID NO: 2 or corresponding to the position is preferably histidine, methionine, serine, leucine, phenylalanine, isoleucine, threonine, asparagine, tryptophan, or glutamine because the catalytic activity for producing an unsaturated hydrocarbon compound tends to even higher in the "decarboxylase according to the present invention," as presented in Examples to be described later. More specifically, when the amino acid at position 395 of the amino acid sequence set forth in SEQ ID NO: 2 or corresponding to the position is glutamine in the "decarboxylase according to the present invention," the amino acid at position 394 of the amino acid sequence set forth in SEQ ID NO: 2 or corresponding to the position is more preferably histidine, methionine, serine, leucine, phenylalanine, isoleucine, threonine, or asparagine, more preferably histidine, methionine, serine, or leucine, and particularly preferably histidine. When the amino acid at position 395 of the amino acid sequence set forth in SEQ ID NO: 2 or corresponding to the position is histidine, the amino acid at position 394 of the amino acid sequence set forth in SEQ ID NO: 2 or corresponding to the position is more preferably is tryptophan, phenylalanine, or histidine. In addition, when the amino acid at position 395 of the amino acid sequence set forth in SEQ ID NO: 2 or corresponding to the position is asparagine, the amino acid at position 394 of the amino acid sequence set forth in SEQ ID NO: 2 or corresponding to the position is more preferably phenylalanine, histidine, leucine, or tryptophan.

In addition, in the "decarboxylase according to the present invention," in addition to the above-mentioned position 395, the further amino acid at position 187 of the amino acid sequence set forth in SEQ ID NO: 2 or corresponding to the position is preferably arginine, lysine, histidine, serine, threonine, glutamine, asparagine, leucine, methionine, or tryptophan, in the same manner as described above. More specifically, when the amino acid at position 395 of the amino acid sequence set forth in SEQ ID NO: 2 or corresponding to the position is glutamine in the "decarboxylase according to the present invention," the amino acid at position 187 of the amino acid sequence set forth in SEQ ID NO: 2 or corresponding to the position is more preferably histidine, leucine, methionine, tryptophan, serine, threonine, asparagine, or arginine, and further preferably histidine, leucine, or methionine. When the amino acid at position 395 of the amino acid sequence set forth in SEQ ID NO: 2 or corresponding to the position is histidine, the amino acid at position 187 of the amino acid sequence set forth in SEQ ID NO: 2 or corresponding to the position is more preferably serine, asparagine, threonine, glutamine, lysine, or leucine, and further preferably serine, asparagine, threonine, or glutamine. When the amino acid at position 395 of an amino acid sequence set forth in SEQ ID NO: 2 or corresponding to the position is asparagine, the amino acid at position 187 of the amino acid sequence set forth in SEQ ID NO: 2 or corresponding to the position is histidine, serine, threonine, or asparagine.

In addition, in the "decarboxylase according to the present invention," in addition to the above-mentioned position 395, the further amino acid at position 327 of the amino acid sequence set forth in SEQ ID NO: 2 or corresponding to the position is preferably leucine.

In addition, in the "decarboxylase according to the present invention," in addition to the above-mentioned position 395, the further amino acid at position 331 of the amino acid sequence set forth in SEQ ID NO: 2 or corresponding to the position is preferably threonine, leucine, methionine, or asparagine. More specifically, when the amino acid at position 395 of the amino acid sequence set forth in SEQ ID NO: 2 or corresponding to the position is glutamine in the "decarboxylase according to the present invention," the amino acid at position 331 of the amino acid sequence set forth in SEQ ID NO: 2 or corresponding to the position is more preferably methionine, leucine, or threonine, and further preferably methionine or leucine. When the amino acid at position 395 of an amino acid sequence set forth in SEQ ID NO: 2 or corresponding to the position is histidine, the amino acid at position 331 of the amino acid sequence set forth in SEQ ID NO: 2 or corresponding to the position is more preferably asparagine.

In addition, in the "decarboxylase according to the present invention," in addition to the above-mentioned position 395, the further amino acid at position 437 of the amino acid sequence set forth in SEQ ID NO: 2 or corresponding to the position is preferably threonine, asparagine, or tyrosine. More specifically, when the amino acid at position 395 of the amino acid sequence set forth in SEQ ID NO: 2 or corresponding to the position is glutamine in the "decarboxylase according to the present invention," the amino acid at position 437 of the amino acid sequence set forth in SEQ ID NO: 2 or corresponding to the position is more preferably tyrosine. When the amino acid at position 395 of an amino acid sequence set forth in SEQ ID NO: 2 or corresponding to the position is histidine, the amino acid at position 437 of the amino acid sequence set forth in SEQ ID NO: 2 or corresponding to the position is more preferably tyrosine.

In addition, in the "decarboxylase according to the present invention," in addition to the above-mentioned position 395, the further amino acid at position 439 of the amino acid sequence set forth in SEQ ID NO: 2 or corresponding to the position is preferably isoleucine or methionine. More specifically, when the amino acid at position 395 of the amino acid sequence set forth in SEQ ID NO: 2 or corresponding to the position is histidine in the "decarboxylase according to the present invention," the amino acid at position 439 of the amino acid sequence set forth in SEQ ID NO: 2 or corresponding to the position is more preferably isoleucine. When the amino acid at position 395 of an amino acid sequence set forth in SEQ ID NO: 2 or corresponding to the position is asparagine, the amino acid at position 439 of the amino acid sequence set forth in SEQ ID NO: 2 or corresponding to the position is more preferably methionine.

In addition, when the amino acid at position 395 of the amino acid sequence set forth in SEQ ID NO: 2 or corresponding to the position is glutamine in the "decarboxylase according to the present invention," the amino acid at position 185 of the amino acid sequence set forth in SEQ ID NO: 2 or corresponding to the position is preferably tyrosine, or the amino acid at position 283 of the amino acid sequence set forth in SEQ ID NO: 2 or corresponding to the position is preferably leucine.

Note that, in the present invention, the "corresponding position" is a position in the same line as threonine at position 395, tyrosine at position 394, and the like in the amino acid sequence set forth in SEQ ID NO: 2 after using a nucleotide and amino acid sequence analysis software (such as GENETYX-MAC or Sequencher) or BLAST (http://blast.ncbi.nlm.nih.gov/Blast.cgi) to align the amino acid sequence set forth in SEQ ID NO: 2 with an amino acid sequence of a ferulic acid decarboxylase or the like derived from another variety.

The "decarboxylase according to the present invention" may be one into which a mutation has been artificially introduced, in addition to the amino acid at position 395 of the amino acid sequence set forth in SEQ ID NO: 2 or corresponding to the position. Specifically, the decarboxylase according to the present invention also includes a "protein composed of an amino acid sequence in which one or more amino acids are replaced, deleted, added, and/or inserted at positions other than position 395 of the amino acid sequence of a ferulic acid decarboxylase (such as the amino acid sequence set forth in SEQ ID NO: 2). Here, "more" is not particularly limited, but is usually 2 to 100, preferably 2 to 50, more preferably 2 to 40, further preferably 2 to 30, more preferably 2 to 20, and further preferably 2 to 10 (for example, 2 to 8, 2 to 4, or 2).

In addition, regarding the decarboxylase according to the present invention, the identity with the amino acid sequence set forth in SEQ ID NO: 2 is preferably 15% or more (for example, 16% or more, 17% or more, 18% or more, or 19% or more), more preferably 20% or more (for example, 30% or more or 40% or more), further preferably 50% or more (for example, 60% or more or 70% or more), more preferably 80% or more (for example, 85% or more, 86% or more, 87% or more, 88% or more, or 89% or more), and more preferably 90% or more (for example, 91% or more, 92% or more, 93% or more, 94% or more, 95% or more, 96% or more, 97% or more, 98% or more, or 99% or more). Note that, in the present invention, the "identity" means the percentage (%) of the number of amino acids that match between the decarboxylase according to the present invention and the amino acid sequence set forth in SEQ ID NO: 2, relative to the total number of amino acids of the decarboxylase according to the present invention.

In addition, whether or not the decarboxylase has catalytic activity for producing an unsaturated hydrocarbon compound can be determined by, for example, directly measuring the amount of unsaturated hydrocarbon compound by gas chromatography mass spectrometry (GC-MS), as presented in Examples to be described later. Moreover, comparison with the amount in the ferulic acid decarboxylase composed of the amino acid sequence set forth in SEQ ID NO: 2 or the wild type ferulic acid decarboxylase makes it possible to determine whether or not the catalytic activity for producing an unsaturated hydrocarbon compound is higher than that of the ferulic acid decarboxylase.

As compared with the ferulic acid decarboxylase composed of the amino acid sequence set forth in SEQ ID NO: 2, the decarboxylase according to the present invention has catalytic activity for producing an unsaturated hydrocarbon compound higher by preferably 2 times or more (for example, 3 times or more, 4 times or more, 5 times or more, 6 times or more, 7 times or more, 8 times or more, or 9 times or more), more preferably 10 times or more (for example, 20 times or more, 30 times or more, or 40 times or more), further preferably 50 times or more (for example, 60 times or more, 70 times or more, 80 times or more, or 90 times or more), more preferably 100 times or more (for example, 200 times or more, 300 times or more, or 400 times or more), more preferably 500 times or more (for example, 600 times or more, 700 times or more, 800 times or more, or 900 times or more), and particularly preferably 1000 times or more.

In addition, as the decarboxylase according to the present invention, it is possible to use only one type of ferulic acid decarboxylase in which the amino acid at position 395 of the amino acid sequence set forth in SEQ ID NO: 2 or corresponding to the position is glutamine or the like, but it is also possible to use two or more types of the decarboxylase according to the present invention in combination. Moreover, as presented in Examples to be described later, from the viewpoint of more easily promoting the decarboxylation of the unsaturated hydrocarbon carboxylic acid compound, one may use in combination a ferulic acid decarboxylase in which the amino acid at position 395 of the amino acid sequence set forth in SEQ ID NO: 2 or corresponding to the position is threonine.

As compared with the wild type ferulic acid decarboxylase, the "ferulic acid decarboxylase modified form" of the present invention has catalytic activity for producing an unsaturated hydrocarbon compound higher by 2 times or more (for example, 3 times or more, 4 times or more, times or more, 6 times or more, 7 times or more, 8 times or more, or 9 times or more), more preferably 10 times or more (for example, 20 times or more, 30 times or more, or times or more), further preferably 50 times or more (for example, 60 times or more, 70 times or more, 80 times or more, or 90 times or more), more preferably 100 times or more (for example, 200 times or more, 300 times or more, or 400 times or more), more preferably 500 times or more (for example, 600 times or more, 700 times or more, 800 times or more, or 900 times or more), and particularly preferably 1000 times or more.

Note that the "wild type ferulic acid decarboxylase" is a ferulic acid decarboxylase before introduction of the modification to the amino acid at position 395 of the amino acid sequence set forth in SEQ ID NO: 2 or corresponding to the position and further the above-mentioned mutation at a different position, and examples thereof include the ferulic acid decarboxylase and natural mutants thereof described in FIGS. 3-8.

The decarboxylase according to the present invention may be added with additional compounds directly or indirectly. Such addition is not particularly limited, and may be addition at the gene level or chemical addition. Further, the addition position is not particularly limited either, and may be one of the amino terminus (hereinafter also referred to as the "N-terminus") and the carboxyl terminus (hereinafter also referred to as the "C-terminus") of the decarboxylase according to the present invention, or may be both of them. The addition at the gene level can be achieved by using a DNA encoding the decarboxylase according to the present invention, the DNA added with a DNA encoding a different protein with matched reading frames. There is no particular limitation on the "different protein" thus added. For the purpose of facilitating the purification of the decarboxylase according to the present invention, a tag protein for purification such as polyhistidine (His-) tag protein, FLAG-tag protein (registered trademark, Sigma-Aldrich), or glutathione-S-transferase (GST) is preferably used. In addition, for the purpose of facilitating the detection of the decarboxylase according to the present invention, a tag protein for detection including a fluorescent protein such as GFP and a chemiluminescent protein such as luciferase is preferably used. The chemical addition may be covalent bond or non-covalent bond. The "covalent bond" is not particularly limited, and examples thereof include an amide bond between an amino group and a carboxyl group, an alkylamine bond between an amino group and an alkyl halide group, a disulfide bond between thiols, and a thioether bond between a thiol group and a maleimide group or an alkyl halide group. Examples of the "non-covalent bond" include a biotin-avidin bond. In addition, as the "additional compounds" thus chemically added, for example, fluorescent dyes such as Cy3 and rhodamine are preferably used for the purpose of facilitating the detection of the decarboxylase according to the present invention.

In addition, the decarboxylase according to the present invention may be used by being mixed with additional components. The additional components are not particularly limited, and examples thereof include sterilized water, physiological saline, vegetable oil, surfactants, lipids, solubilizers, buffer agents, protease inhibitors, and preservatives.

<DNA Encoding Decarboxylase According to Present Invention and Vector Having the DNA>

Next, description is provided for e.g. a DNA encoding the decarboxylase according to the present invention. Introduction of such DNA makes it possible to transform the host cell, produce the decarboxylase according to the present invention in the cell, and further produce the unsaturated hydrocarbon compound.

The DNA according to the present invention may be, as long as it encodes the above-mentioned decarboxylase according to the present invention, a natural DNA, a DNA obtained by artificially introducing a mutation into a natural DNA, or a DNA composed of an artificially designed nucleotide sequence. Moreover, the form thereof is not particularly limited, and includes a cDNA as well as a genomic DNA and a chemically synthesized DNA. These DNAs can be prepared by those skilled in the art using conventional means. The genomic DNA can be prepared, for example, as follows. Specifically, a genomic DNA is extracted from *Aspergillus niger* or the like to create a genomic library (as a vector, plasmid, phage, cosmid, BAC, PAC, or the like can be used). This is developed, and colony hybridization or plaque hybridization is performed using a probe prepared based on the nucleotide sequence of the ferulic acid decarboxylase gene (for example, the nucleotide sequence set forth in SEQ ID NO: 1). In addition, it is also possible to prepare a genomic DNA by preparing a primer specific to the ferulic acid decarboxylase gene and performing PCR using this primer. In addition, a cDNA can be prepared, for example, as follows. Specifically, an mRNA extracted from *Aspergillus niger* or the like is used as a basis to synthesize a cDNA, which is inserted into a vector such as λZAP to prepare a cDNA library. This is developed, and colony hybridization or plaque hybridization, or PCR is performed in the same manner as described above.

Then, those skilled in the art can introduce, if necessary, a mutation of substituting glutamine or the like for the amino acid at position 395 of the amino acid sequence set forth in SEQ ID NO: 2 or corresponding to the position into the DNA thus prepared by using a known site-specific mutagenesis. Examples of site-specific mutagenesis include the Kunkel method (Kunkel, T. A., Proc Natl Acad Sci USA, 1985, Volume 82, issue 2, pages 488 to 492) and the SOE (splicing-by-overlap-extension)-PCR method (Ho, S. N., Hunt, H. D., Horton, R. M., Pullen, J. K., and Pease, L. R., Gene, 1989, Volume 77, pages 51 to 59).

In addition, those skilled in the art can artificially design a nucleotide sequence encoding a protein in which the amino acid at position 395 of a ferulic acid decarboxylase or corresponding to the position is replaced with glutamine or the like, and use an automatic nucleic acid synthesizer based on the sequence information to chemically synthesize the DNA according to the present invention.

Moreover, from the viewpoint of further improving the expression efficiency of the encoded decarboxylase according to the present invention in the host cell, the DNA according to the present invention may can the form of a DNA encoding the decarboxylase according to the present invention in which the codon is optimized in accordance with the type of the host cell.

In addition, in order to make it possible to replicate the above-mentioned DNA in the host cell, the present invention can take the form of a vector inserted with the DNA.

In the present invention, the "vector" can be constructed based on, for example, a plasmid, which exists as a self-replicating vector, that is, an extrachromosomal independent entity whose replication is independent of chromosomal replication. In addition, a vector may be one that, when introduced into a host cell, is integrated into the genome of the host cell and replicated together with the chromosome into which it has been integrated.

Examples of such vector include plasmids and phage DNAs. In addition, examples of the plasmids include plasmids derived from *E. coli* (such as pET22, pBR322, pBR325, pUC118, pUC119, pUC18, and pUC19), plasmids derived from yeast (such as YEp13, YEp24, and YCp50), and plasmids derived from *Bacillus subtilis* (such as pUB110 and pTP5). Examples of the phage DNAs include λ phages (such as Charon4A, Charon21A, EMBL3, EMBL4, Δgt10, Δgt11, and λZAP). Furthermore, as a vector according to the present invention, an insect virus vector such as a baculovirus can be used when the host cell is derived from an insect, T-DNA or the like can be used when the host cell is derived from a plant, and an animal virus vector such as a retrovirus or an adenovirus vector can also be used when the host cell is derived from an animal. In addition, as a vector construction procedure and method according to the present invention, ones conventionally used in the field of genetic engineering can be used. For example, in order to insert the DNA according to the present invention into a vector, a method is employed in which a purified DNA is first cleaved with an appropriate restriction enzyme, inserted into a restriction enzyme site or a multicloning site of an appropriate vector, and ligated to the vector.

In addition, the vector according to the present invention may be in the form of an expression vector containing the decarboxylase according to the present invention encoded by the DNA in a state capable of expression in a host cell. For the purpose of introduction into a host cell to express the decarboxylase according to the present invention, the "expression vector" according to the present invention preferably contains, in addition to the DNA, a DNA sequence for controlling the expression, a genetic marker for selecting a transformed host cell, and the like. Examples of the DNA sequence for controlling expression include promoters, enhancers, splicing signals, poly A addition signals, ribosome binding sequences (SD sequences), and terminators. The promoters are not particularly limited as long as they exhibit transcriptional activity in the host cell, and can be obtained as a DNA sequence which controls the expression of a gene encoding a protein that is of a type same as or different from the host cell. In addition to the DNA sequence which controls expression, a DNA sequence which induces expression may be contained. When the host cell is a bacterium, examples of such DNA sequence which induces expression include the lactose operon, which can induce expression of a gene located downstream by the addition of isopropyl-β-D-thiogalactopyranoside (IPTG). The gene marker in the present invention may be appropriately selected according to the method of selecting a transformed host cell. For example, it is possible to use a gene encoding drug resistance and a gene complementary to auxotrophy.

In addition, the DNA or vector according to the present invention may be used by being mixed with additional components. The additional components are not particularly limited, and examples thereof include sterilized water, physiological saline, vegetable oil, surfactants, lipids, solubilizers, buffer agents, DNase inhibitors, and preservatives.

<Agent for Promoting Production of Unsaturated Hydrocarbon Compound>

As described above, use of the decarboxylase according to the present invention, a DNA encoding the decarboxylase, or a vector inserted with the DNA makes it possible to decarboxylate the unsaturated hydrocarbon dicarboxylic acid compound represented by the formula (1) or (3) or the geometric isomer thereof, and promote the production of the unsaturated hydrocarbon compound represented by the formula (2) or (5) or the geometric isomer thereof.

Therefore, the present invention provides an agent for promoting production of the unsaturated hydrocarbon compound represented by the formula (2) or the geometric isomer thereof by decarboxylating the unsaturated hydrocarbon dicarboxylic acid compound represented by the formula (1) or the geometric isomer thereof, or an agent for promoting production of the unsaturated hydrocarbon compound represented by the formula (5) or the geometric isomer thereof by decarboxylating the unsaturated hydrocarbon dicarboxylic acid compound represented by the formula (3) or the geometric isomer thereof, the agent comprising: a ferulic acid decarboxylase in which an amino acid at position 395 of an amino acid sequence set forth in SEQ ID NO: 2 or corresponding to the position is glutamine or the like; a DNA encoding the ferulic acid decarboxylase; or a vector inserted with the DNA.

Such an agent may be one containing the decarboxylase according to the present invention, but may be used by being mixed with additional components. Such additional components are not particularly limited, and examples thereof include sterilized water, physiological saline, vegetable oil, surfactants, lipids, solubilizers, buffer agents, protease inhibitors, DNase inhibitors, and preservatives.

The present invention can also provide a kit including such an agent. In the kit of the present invention, the agent may be included in the form of a host cell described later into which the DNA or the like according to the present invention has been introduced and transformed. Moreover, in addition to such an agent, the kit of the present invention may include the compound represented by the formula (1) or (3) or the geometric isomer thereof, a host cell for introducing the DNA or the like according to the present invention, a medium for culturing the host cell, an instruction manual for use thereof, and the like. Moreover, such an instruction manual is a manual for using the agent of the present invention and the like in the method for producing the above-mentioned unsaturated hydrocarbon compound. The manual can include, for example, information on the experimental method and experimental conditions for the production method of the present invention, the agent of the present invention, and the like (for example, information such as a vector map showing the nucleotide sequence of a vector, sequence information on the decarboxylase according to the present invention, information on the origin and properties of the host cell as well as the culture conditions of the host cell, and the like).

<Host Cell Introduced with DNA Encoding Decarboxylase According to Present Invention, and the Like>

Next, description is provided for a host cell introduced with the DNA or vector according to the present invention. Use of a host cell transformed by the introduction of the above-mentioned DNA or vector makes it possible to produce the decarboxylase according to the present invention, and makes it possible to further produce the unsaturated hydrocarbon compound represented by the formula (2) or (5) or the geometric isomer thereof.

The host cell introduced with the DNA or vector according to the present invention is not particularly limited, and examples thereof include microorganisms (such as *E. coli*, budding yeast, fission yeast, *Bacillus subtilis*, actinomycetes, and filamentous fungi), plant cells, insect cells, and animal cells. However, it is preferable to use a microorganism, and it is more preferable to use *E. coli* as a host cell from the viewpoint that it is possible to contribute to the production of the unsaturated hydrocarbon compound represented by the formula (2) or (5) or the geometric isomer thereof with a relatively inexpensive medium, with high proliferation properties in a short time, and further with high productivity.

In addition, the host cell introduced with the DNA or vector according to the present invention is preferably a cell which retains a flavin prenyltransferase from the viewpoint of inducing prenylation of flavin mononucleotide (FMN) and producing prFMN or an isomer thereof which contributes to improving the productivity of the unsaturated hydrocarbon compound represented by the formula (2) or (5) or the geometric isomer thereof.

In addition, in the production of butadiene, the host cell introduced with the DNA or vector according to the present invention is preferably a cell having an activated pathway for biosynthesizing muconic acid from glucose via 3-dehydroshikimic acid and catechol from the viewpoint of easily producing muconic acid, which is a substrate of the decarboxylase according to the present invention, from glucose as a raw material. Examples of such a cell include a having an enzyme which makes it possible to suppress the activities of phosphotransferase-based enzymes and pyruvate kinase and synthesize an aromatic compound from chorismic acid or isochorismic acid (for example, the microorganism described in International Publication No. WO2017/033965), *E. coli* described in Kruyer N S et al., Curr Opin Biotechnol. 2017, June; 45: pages 136 to 143, *Pseudomonas putida*, or budding yeast.

The introduction of the DNA or vector according to the present invention can be carried out according to a method conventionally used in this field. Examples of the method for introduction into microorganisms such as *E. coli* include the heat shock method, the electroporation method, the spheroplast method, and the lithium acetate method, examples of the method for introduction into plant cells include a method using *Agrobacterium* and the particle gun method, examples of the method for introduction into insect cells include a method using baculovirus and the electroporation method, and examples of the method for introduction into animal cells include the calcium phosphate method, the lipofection method, and the electroporation method.

The DNA or the like thus introduced into the host cell may be, in the host cell, retained by being randomly inserted into its genomic DNA, may be retained by homologous recombination, and can be, in the case of a vector, replicated and retained as an independent entity outside the genomic DNA.

In addition, regarding the host cell introduced with the DNA or vector according to the present invention, the catalytic activity for producing 1,3-butadiene, measured by the method presented in Examples to be described later, is preferably 5 μM or more (for example, 10 μM or more, 20 μM or more, 30 μM or more, or 40 μM or more), more preferably 50 μM or more (for example, 60 μM or more, 70 μM or more, 80 μM, or 90 μM), more preferably 100 μM or more (for example, 150 μM or more, 200 μM or more, 300 μM or more, or 400 μM or more), more preferably 500 μM or more (for example, 600 μM or more, 700 μM or more, 800 μM or more, or 900 μM or more), and particularly preferably 1 mM or more.

<Method for Producing Ferulic Acid Decarboxylase Modified Form of Present Invention>

As presented in Examples to be described later, culturing of a host cell introduced with a DNA or the like encoding the ferulic acid decarboxylase modified form of the present invention makes it possible to produce a ferulic acid decarboxylase modified form in the host cell.

Therefore, the present invention can provide a method including culturing a host cell introduced with a DNA encoding the ferulic acid decarboxylase modified form of the present invention or a vector containing the DNA, and collecting a protein expressed in the host cell.

In the present invention, the conditions for "culturing a host cell" may be any conditions as long as the host cell can produce the ferulic acid decarboxylase modified form of the present invention, and according to the type of the host cell, the medium used, and the like, those skilled in the art can appropriately adjust and set the temperature, the presence or absence of addition of air, the concentration of oxygen, the concentration of carbon dioxide, the pH of the medium, the culture temperature, the culture time, the humidity, and the like.

Such a medium only needs to have a content which can be used as a nutrient source by the host cell, and examples of the content include carbon sources, nitrogen sources, sulfur sources, inorganic salts, metals, peptones, yeast extracts, meat extracts, casein hydrolysates, and serum. In addition, such a medium may be added with, for example, IPTG for inducing the expression of a DNA encoding the ferulic acid decarboxylase modified form of the present invention, an antibiotic corresponding to the drug resistance gene which can be encoded by the vector according to the present invention (for example, ampicillin), or a nutrient corresponding to a gene complementing the auxotrophy which can be encoded by the vector according to the present invention (for example, arginine or histidine).

Additionally, examples of the method for "collecting a protein expressed in the host cell" from the host cell thus cultured include a method in which the host cell is recovered from the medium by filtration, centrifugation, or the like, the recovered host cell is treated by cell lysis, grinding treatment, or pressure crushing, and further, the protein expressed in the host cell is purified and concentrated by ultrafiltration treatment, salting out, solvent precipitation such as ammonium sulfate precipitation, chromatography (such as gel chromatography, ion exchange chromatography, or affinity chromatography), or the like. Moreover, when the ferulic acid decarboxylase modified form of the present invention is added with the above-mentioned purified tag protein, it can be purified and collected using a substrate to which the tag protein is adsorbed. Furthermore, these purification and concentration methods may be carried out alone or may be carried out in multiple steps in appropriate combination.

In addition, the ferulic acid decarboxylase modified form of the present invention is not limited to the above-described biological synthesis, and can also be produced using the DNA or the like of the present invention and a cell-free protein synthesis system. Such a cell-free protein synthesis system is not particularly limited, and examples thereof include synthesis systems derived from wheat germ, *E. coli*, rabbit reticulocytes, and insect cells. Moreover, those skilled in the art can chemically synthesize the ferulic acid decarboxylase modified form of the present invention using a commercially available peptide synthesizer or the like.

In addition, the present invention can also provide a method for producing a ferulic acid decarboxylase with enhanced catalytic activity for producing the unsaturated hydrocarbon compound represented by the formula (2) or (5) or the geometric isomer thereof, the method including modifying, in a ferulic acid decarboxylase, the amino acid at position 395 of the amino acid sequence set forth in SEQ ID NO: 2 or corresponding to the position to glutamine or the like, and preferably further modifying an amino acid at a different position (such as the above-mentioned amino acid at position 394 of the amino acid sequence set forth in SEQ ID NO: 2 or corresponding to the position).

The "ferulic acid decarboxylase with enhanced catalytic activity for producing the unsaturated hydrocarbon compound represented by the formula (2) or (5) or the geometric isomer thereof" means a ferulic acid decarboxylase having a high catalytic activity for producing an unsaturated hydrocarbon compound as compared with that before the introduction of a mutation into the amino acid at position 395 of the amino acid sequence set forth in SEQ ID NO: 2 or corresponding to the position and preferably the further introduction of a mutation into the amino acid at the different position, and the comparison targets are usually ferulic acid decarboxylases derived from various organisms such as *Aspergillus niger* above and natural mutants thereof.

Note that, for a preferable embodiment of the mutation 26 introduced into the amino acid at position 395 of the amino acid sequence set forth in SEQ ID NO: 2 or corresponding to the position, or the amino acid at the different position (such as the amino acid at position 394 of the amino acid sequence set forth in SEQ ID NO: 2 or corresponding to the position), that is, the replacement with glutamine or the like or histidine or the like, see the description of <Decarboxylase According to Present Invention> mentioned above.

The "modification to glutamine or the like or histidine or the like" in the ferulic acid decarboxylase can be performed by modification of the encoding DNA. As described above, regarding the "modification of the DNA," such DNA modification can be appropriately performed by those skilled in the art using a known method such as site-directed mutagenesis or DNA chemical synthesis based on the modified sequence information. In addition, the "modification to glutamine or the like or histidine or the like" can also be performed using a peptide chemical synthesis method as described above.

In addition, it can be evaluated by GC-MS analysis or the like whether or not such mutagenesis has enhanced the catalytic activity for producing an olefin compound, as described above.

Preferred embodiments of the present invention have been described above, but the amino acid in the ferulic acid decarboxylase according to the present invention is not limited to the above-mentioned amino acid at position 395 of the amino acid sequence set forth in SEQ ID NO: 2 or corresponding to the position.

As presented in the following Examples, the catalytic activity for producing an unsaturated hydrocarbon compound is higher than that of the wild type when position 394 of the amino acid sequence set forth in SEQ ID NO: 2 is phenylalanine, methionine, tryptophan, leucine, isoleucine, or the like. In addition, similarly, the catalytic activity increases when position 437 of the amino acid sequence set forth in SEQ ID NO: 2 is tyrosine.

Therefore, the present invention can also provide, in place of the above-mentioned ferulic acid decarboxylase in which the amino acid at position 395 of the amino acid sequence set forth in SEQ ID NO: 2 or corresponding to the position is glutamine or the like, at least one ferulic acid decarboxylase selected from (a) a ferulic acid decarboxylase in which an amino acid at position 395 of an amino acid sequence set forth in SEQ ID NO: 2 or corresponding to the position is glutamine, histidine, asparagine, leucine, isoleucine, methionine, lysine, serine, arginine, tyrosine, or phenylalanine, (b) a ferulic acid decarboxylase in which an amino acid at position 394 of the amino acid sequence set forth in SEQ ID NO: 2 or corresponding to the position is phenylalanine, methionine, tryptophan, leucine, isoleucine, histidine, threonine, arginine, or asparagine, and (c) a ferulic acid decarboxylase in which an amino acid at position 437 of the amino acid sequence set forth in SEQ ID NO: 2 or corresponding to the position is tyrosine, and an embodiment using the ferulic acid decarboxylase.

In addition, similarly, the present invention can provide, in place of the above-mentioned embodiment relating to the modification of the amino acid at position 395 of the amino acid sequence set forth in SEQ ID NO: 2 or corresponding to the position to glutamine or the like, an embodiment relating to at least one modification selected from the following (d) to (f)

(d) a ferulic acid decarboxylase such that an amino acid at position 395 of an amino acid sequence set forth in SEQ ID NO: 2 or corresponding to the position is modified to glutamine, histidine, asparagine, leucine, isoleucine, methionine, lysine, serine, arginine, tyrosine, or phenylalanine, (e) an amino acid at position 394 of the amino acid sequence set forth in SEQ ID NO: 2 or corresponding to the position is modified to phenylalanine, methionine, tryptophan, leucine, isoleucine, histidine, threonine, arginine, or asparagine, and (f) an amino acid at position 437 of the amino acid sequence set forth in SEQ ID NO: 2 or corresponding to the position is modified to tyrosine.

EXAMPLES

Hereinafter, the present invention is described more specifically based on Examples, but the present invention is not limited to the following Examples.

Example 1

<Preparation and Evaluation of Ferulic Acid Decarboxylase Modified Form>

In order to make it possible to produce butadiene (1,3-butadiene) with high productivity, the present inventors have arrived at an idea of producing 1,3-butadiene by introducing a mutation into an amino acid of a ferulic acid decarboxylase (hereinafter also referred to as "FDC") which catalyzes the production reaction of the following 4-vinylguaiacol (4VG) and changing the substrate specificity of the enzyme (ferulic acid decarboxylase modified form) from that to the original ferulic acid to that to cis, cis-muconic acid.

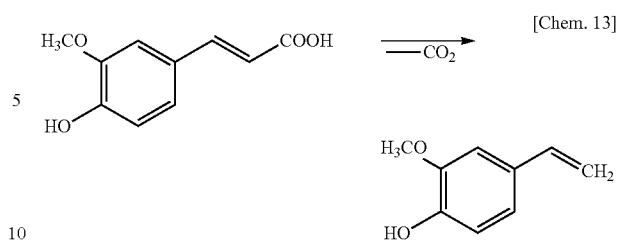

[Chem. 13]

Specifically, the present inventors have arrived at an idea of producing an unsaturated hydrocarbon compound such as butadiene through a decarboxylation reaction as represented by the following formula by introducing a mutation into an amino acid of a ferulic acid decarboxylase and changing the substrate specificity of the enzyme from that to the original ferulic acid to that to muconic acid or the like.

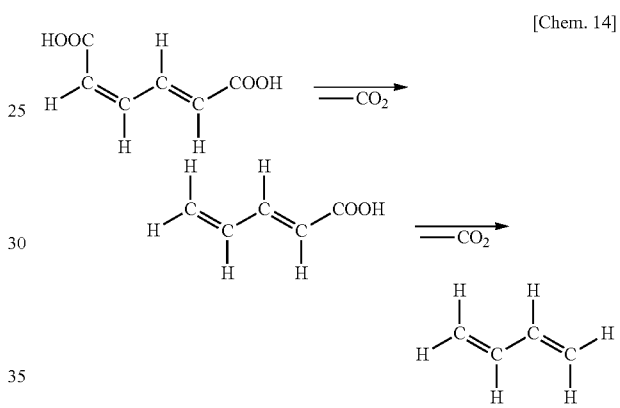

[Chem. 14]

To this end, the present inventors used the method presented below or the like to introduce mutations involving amino acid replacement into various positions of a ferulic acid decarboxylase, and prepared multiple ferulic acid decarboxylase modified forms. Then, the present inventors evaluated these modified forms in terms of catalytic activity for the production of 1,3-butadiene using cis,cis-muconic acid as a substrate.

<Preparation of Plasmid Vector>

First, in order to efficiently express *Aspergillus niger*-derived FDC in *E. coli*, in a form where the C-terminus of the wild type nucleotide sequence encoding it was fused with a polyhistidine tag, the frequency of codon usage in *E. coli* was considered to perform modification. Subsequently, a DNA composed of such a modified nucleotide sequence was chemically synthesized according to a conventional method. Then, the DNA thus prepared and the pET22b(+) vector (manufactured by Novagen) were ligated by the Gibson Assembly method (using a kit of New England Biolabs, NEBuilder HiFi DNA Assembly Master Mix (registered trademark)), to thereby prepare a plasmid vector (FDC vector) capable of expressing the wild type FDC in *E. coli*. Similarly, the pColADuet vector (manufactured by Novagen) and a DNA obtained by amplifying a gene encoding flavin prenyltransferase (hereinafter also referred to as "UbiX") from *E. coli* (K-12) strain by the Polymerase Chain Reaction method were ligated by the Gibson Assembly method, to thereby prepare a plasmid vector (UbiX vector) capable of expressing the wild type UbiX in *E. coli*.

Next, in order to introduce a mutation involving amino acid replacement into a ferulic acid decarboxylase at each of the 10 positions of FDC as presented in Table 7 below, primer encoding the amino acid sequence introduced with the mutations were designed and synthesized.

TABLE 7

| Amino Acid Position | Amino Acid Before Replacement | Amino Acid After Replacement |
|---|---|---|
| 185 | L | R, K, H, T, Q, N, I, M, F, Y, W |
| 187 | I | R, K, H, T, Q, N, L, M, F, Y, W |
| 283 | M | R, K, H, T, Q, N, I, L, F, Y, W |
| 323 | T | R, K, H, Q, N, I, L, M, F, Y, W |
| 327 | I | R, K, H, T, Q, N, L, M, F, Y, W |
| 331 | A | R, K, H, T, Q, N, I, L, M, F, Y, W |
| 394 | Y | R, K, H, T, Q, N, I, L, M, F, W |
| 395 | T | R, K, H, Q, N, I, L, M, F, Y, W |
| 437 | F | R, K, H, T, Q, N, I, L, M, Y, W |
| 439 | L | R, K, H, T, Q, N, I, M, F, Y, W |

Then, the primers were used with the FDC vector as a template to prepare FDCs introduced with the mutations according to the protocol of the Gibson Assembly method, and plasmid vectors (FDC modified form vectors) expressible in *E. coli* were prepared in a form where their C-terminus was fused with a polyhistidine tag.

In addition, using the FDC modified form vectors as a template, the genes encoding the FDC modified forms were amplified by PCR. Next, the obtained amplification products were ligated to FDC vectors by the Gibson Assembly method, to thereby also prepare plasmid vectors (FDCDuet vectors) capable of co-expressing wild type FDC and mutant FDC in *E. coli*.

<Preparation of Enzyme Reaction Solution and Measurement of Enzyme Activity>

The vectors prepared as described above (5 μg of FDC vector or FDC modified form vector, and 5 μg of UbiX vector) were introduced into *E. coli* C41 (DE3) strain (manufactured by Lucigen Corporation, 100 μL) by the heat shock method to prepare a transformant co-expressing wild type FDC or the FDC modified forms and UbiX. In addition, in the same manner as above, the FDCDuet vector and the UbiX vector (each 5 μg) were introduced into 100 μL of *E. coli* C41 (DE3) strain to also prepare a transformant co-expressing wild type FDC, the FDC modified forms, and UbiX.

Then, each of these transformants was cultured for 6 hours in an LB medium supplemented with ampicillin and kanamycin. It should be noted that the growth of these transformants reaches a peak after such 6-hour culture (pre-culture). For this reason, the amount of bacterial cells at the start of the enzyme reaction to be described later is uniform among these transformants.

In addition, to 12 g/L tryptone, 24 g/L yeast extract, 10 g/L glycerol, 9.4 g/L dipotassium hydrogen phosphate, 2.2 g/L potassium dihydrogen phosphate, 20 g/L lactose, 100 mg/L ampicillin, and 50 mg/L kanamycin, the substrate cis,cis-muconic acid (manufactured by Sigma-Aldrich) was added to a final concentration of 0.5 mM, to thereby prepare an enzyme reaction medium.

Then, to a 10 mL vial for a headspace type gas chromatography mass spectrometer (HS/GSMS), 100 μL of the *E. coli* culture solution cultured for 6 hours and 2.5 mL of the enzyme reaction medium were added, and immediately after that, the cap of the vial was closed, followed by further culture at 37° C. and a shaking rate of 180 rpm. The peak areas representing the amount of 1,3-butadiene produced in the headspace of the vial 18 hours after the start of the culture were measured by GC-MS (manufactured by Shimadzu Corporation under the trade name: GCMS-QP Ultra).

Figure 2:
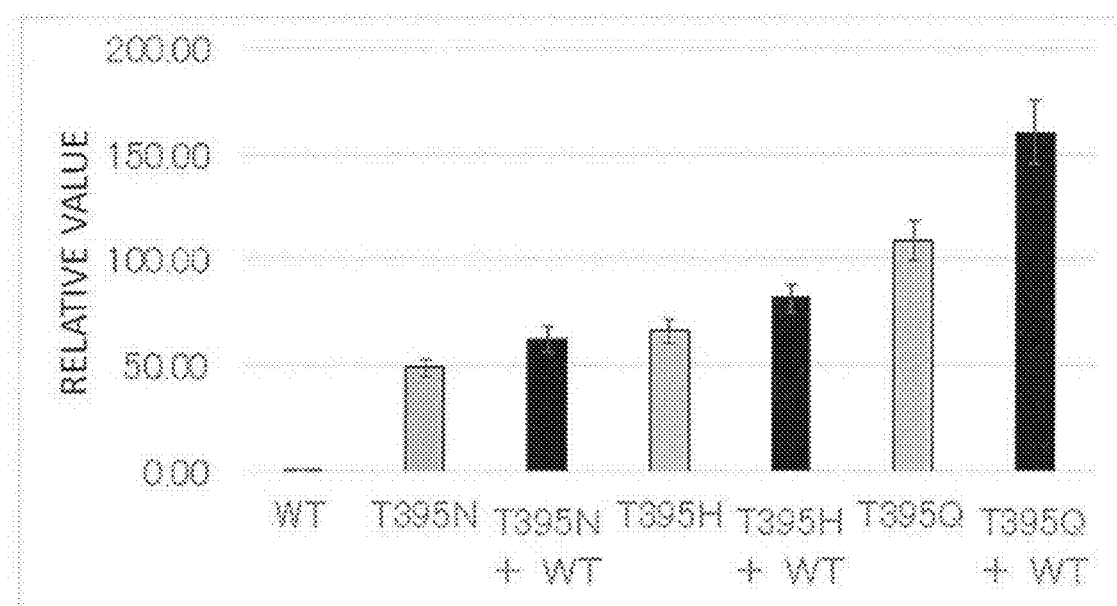
FIG. 2 is a graph which relates to *E. coli* expressing a ferulic acid decarboxylase modified form (T395N, T395H, or T395Q) or each modified form with a wild type ferulic acid decarboxylase, and illustrates the results of analyzing the catalytic activity for producing 1,3-butadiene using cis,cis-muconic acid as a substrate. In the figure, the vertical axis represents the relative value calculated from the amount of 1,3-butadiene produced by each ferulic acid decarboxylase modified form or each modified form with a wild type ferulic acid decarboxylase where the wild type ferulic acid decarboxylase (WT) is a reference (1).

Table 8 and FIGS. 1 and 2 present the relative value of 1,3-butadiene production in each of the FDC modified forms relative to wild type FDC, calculated based on the obtained peak areas. In addition, the 1,3-butadiene production (concentration of 1,3-butadiene in the enzyme reaction medium) was calculated based on the peak area obtained from the standard sample with the vial cap closed immediately after adding, to a 10 mL vial for HS/GSMS, 2.5 mL of the enzyme reaction medium added with 1,3-butadiene (manufactured by Tokyo Chemical Industry Co., Ltd.). Table 9 presents the obtained results.

TABLE 8

| Relative Value for Wild Type (WT) | | Replacement Position | | | | | | | | | |
|---|---|---|---|---|---|---|---|---|---|---|---|
| | | L185 | I187 | M283 | T323 | I327 | A331 | Y394 | T395 | F437 | L439 |
| Amino Acid After Replacement | R | 0.1 | 1.6 | 0 | 0 | 0 | 0 | 3.6 | 4.3 | 0 | 0 |
| | K | 0.1 | 0.3 | 0 | 0 | 0 | 0 | 0.2 | 13.3 | 0 | 0.2 |
| | H | 2.4 | 6.4 | 0 | 0 | 0 | 1 | 6.3 | 66.4 | 0.1 | 0 |
| | S | 1.9 | 2.3 | 0 | 1 | 0.1 | 1.1 | 1.4 | 5 | 0.1 | 0.1 |
| | T | 0.2 | 3.5 | 0.3 | WT | 0.1 | 5.5 | 4.3 | WT | 0 | 0.1 |
| | Q | 0.4 | 4 | 0.1 | 0 | 0.1 | 1.2 | 2 | 109 | 0.1 | 0 |
| | N | 0.8 | 1.9 | 0 | 0 | 0.1 | 1.5 | 3.3 | 49 | 0.7 | 0 |
| | I | 0.8 | WT | 1.2 | 0 | WT | 3.1 | 9.7 | 16.8 | 0.1 | 3.5 |
| | L | WT | 1.7 | 6.5 | 0 | 4.4 | 3.4 | 15.5 | 28.5 | 0.2 | WT |
| | M | 0.8 | 1.9 | WT | 0 | 9.2 | 7.2 | 22 | 15.6 | 2 | 5.3 |
| | F | 2 | 4.2 | 3.4 | 0 | 0.6 | 0.3 | 32.7 | 2.8 | WT | 3.4 |
| | Y | 2.1 | 1 | 2.9 | 0 | 2.7 | 1.7 | WT | 3.2 | 41.2 | 1.4 |
| | W | 1.9 | 0 | 0.1 | 0 | 0 | 0 | 18.3 | 0.3 | 0.9 | 0.1 |

TABLE 9

| | WT | T395R | T395S | T395K | T395N | T395H | T395Q |
|---|---|---|---|---|---|---|---|
| WT (−) | 1.39 μM | 6.01 μM | 6.95 μM | 18.54 μM | 68.06 μM | 92.17 μM | 151.44 μM |
| WT (+) | — | — | — | — | 86.67 μM | 114.04 μM | 222.80 μM |

As presented in Table 8 and FIG. 1, it was revealed that, at position 395 among the 10 positions introduced with mutations, replacement of the threonine at the position with a different amino acid (glutamine, histidine, asparagine, leucine, isoleucine, methionine, lysine, serine, arginine, tyrosine, or phenylalanine) generally improved the catalytic activity for the production of 1,3-butadiene (improved the catalytic activity by at least about 3 times as compared with wild type FDC). Surprisingly, the catalytic activity for the production of 1,3-butadiene was improved by nearly 50 times in the case of replacing position 395 with asparagine, nearly 70 times in the case of replacement with histidine, and particularly surprisingly, 100 times or more in the case of replacement with glutamine as compared with wild type FDC.

In addition, as presented in Table 9 and FIG. 2, the catalytic activity for the production of 1,3-butadiene thus improved was further increased by using wild type FDC in combination.

In addition, as presented in Table 8 and FIG. 1, it was also revealed that the catalytic activity of a ferulic acid decarboxylase for the production of 1,3-butadiene was improved as compared with the wild type also in the case of replacing only the tyrosine at position 394 with a different amino acid (phenylalanine, methionine, tryptophan, leucine, isoleucine, histidine, threonine, arginine, or asparagine) and in the case of replacing only the phenylalanine at position 437 with tyrosine, in addition to the amino acid replacement at position 395 mentioned above.

Example 2

<Production and Evaluation of Ferulic Acid Decarboxylase Double Amino Acid Modified Form>

In each of the modified forms in which position 395 of ferulic acid decarboxylase had been replaced with glutamine, histidine, or asparagine (also referred to as "T395Q," "T395H," or "T395N," respectively), a mutation involving amino acid replacement was further introduced into a different position in the same manner as described in Example 1 to prepare a ferulic acid decarboxylase double amino acid modified form. Then, these modified products were evaluated in terms of the catalytic activity for the production of 1,3-butadiene using cis,cis-muconic acid as a substrate. Tables 10 to 12 presents the obtained results for further amino acid modified forms of "T395Q", "T395H," and "T395N", respectively.

TABLE 10

| Relative Value for Wild Type (WT) | | Further Replacement Position in T395Q | | | | | | | | |
|---|---|---|---|---|---|---|---|---|---|---|
| | | L185 | I187 | M283 | T323 | I327 | A331 | Y394 | F437 | L439 |
| Amino Acid After Replacement | R | 0 | 130.8 | 0 | 0 | 0 | 0 | 87.2 | 0 | 0 |
| | K | 0 | 43.6 | 0 | 0 | 0 | 0 | 0 | 0 | 0 |
| | H | 0 | 250.7 | 0 | 0 | 0 | 54.5 | 1002.6 | 0 | 0 |
| | S | 21.8 | 141.7 | 0 | 32.7 | 0 | 32.7 | 501.4 | 0 | 0 |
| | T | 0 | 141.7 | 0 | WT | 0 | 119.9 | 425.1 | 0 | 0 |
| | Q | 0 | 218 | 0 | 0 | 0 | 54.5 | 207.1 | 0 | 10.9 |
| | N | 0 | 141.7 | 0 | 0 | 0 | 10.9 | 302.4 | 43.6 | 0 |
| | I | 109 | WT | 0 | 0 | WT | 109 | 457.8 | 0 | 239.8 |
| | L | WT | 218 | 196.2 | 0 | 305.2 | 218 | 501.4 | 0 | WT |
| | M | 109 | 218 | WT | 0 | 21.8 | 261.6 | 686.8 | 21.8 | 239.8 |
| | F | 65.4 | 43.6 | 0 | 0 | 0 | 65.4 | 479.6 | WT | 21.8 |
| | Y | 130.8 | 21.8 | 21.8 | 0 | 0 | 21.8 | WT | 130.8 | 0 |
| | W | 0 | 174.4 | 0 | 0 | 0 | 0 | 261.6 | 0 | 0 |

TABLE 11

| Relative Value for Wild Type (WT) | | Further Replacement Position in T395H | | | | | | | | |
|---|---|---|---|---|---|---|---|---|---|---|
| | | L185 | I187 | M283 | T323 | I327 | A331 | Y394 | F437 | L439 |
| Amino Acid After Replacement | R | 0 | 22.7 | 0 | 0 | 0 | 0 | 6.7 | 0.2 | 0 |
| | K | 0.3 | 117.7 | 0 | 0 | 0.7 | 0 | 0.4 | 0 | 0 |
| | H | 39.2 | 0 | 0 | 0 | 0 | 27.9 | 156.2 | 1.6 | 1.2 |
| | S | 24.1 | 368.1 | 0.2 | 24.1 | 1.1 | 33.2 | 82.6 | 1 | 0.3 |
| | T | 8.6 | 162.7 | 0 | 0 | 0 | 39.8 | 60.2 | 121.1 | 0.3 |
| | Q | 4.5 | 146.1 | 0.1 | 0 | 2 | 16.1 | 29.5 | 58.6 | 3.3 |
| | N | 10.1 | 363.6 | 0 | 0 | 13.3 | 90.3 | 78.1 | 96.2 | 2.8 |
| | I | 66.4 | WT | 6.6 | 0 | WT | 19.9 | 93 | 0 | 146.1 |
| | L | WT | 106.2 | 53.1 | 0 | 232.4 | 93 | 59.6 | 33.2 | WT |
| | M | 19.9 | 66.4 | WT | 0 | 39.8 | 46.6 | 39.8 | 39.8 | 79.7 |
| | F | 6.6 | 39.8 | 0 | 0 | 0 | 0 | 285.5 | WT | 0 |
| | Y | 33.2 | 39.8 | 6.6 | 0 | 6.6 | 0 | WT | 232.4 | 0 |
| | W | 6.6 | 33.2 | 0 | 0 | 0 | 0 | 325.4 | 19.9 | 0 |

TABLE 12

| Relative Value for Wild Type (WT) | | Further Replacement Position in T395N | | | | | | | | |
|---|---|---|---|---|---|---|---|---|---|---|
| | | L185 | I187 | M283 | T323 | I327 | A331 | Y394 | F437 | L439 |
| Amino Acid After Replacement | R | 0 | 48.4 | 0 | 0 | 0 | 0 | 4.1 | 4.1 | 0 |
| | K | 0 | 6.6 | 0 | 0 | 0 | 0 | 3.4 | 0.4 | 0 |
| | H | 0 | 92.4 | 0 | 0 | 0 | 22.2 | 132.1 | 0.9 | 0 |
| | S | 8.8 | 52.8 | 0 | 13.2 | 0 | 35.2 | 44.1 | 0.2 | 0 |
| | T | 0 | 62.8 | 0 | WT | 0 | 39.2 | 48.4 | 88 | 0.2 |
| | Q | 0 | 66 | 0 | 0 | 0 | 0.1 | 52.8 | 4 | 0.4 |
| | N | 0 | 57.2 | 0 | 0 | 0 | 2.1 | 39.2 | 88 | 0.3 |
| | I | 44 | WT | 0 | 0 | WT | 8.5 | 52.8 | 0 | 17.6 |
| | L | WT | 35.2 | 26.4 | 0 | 101.2 | 1736 | 96.8 | 0 | WT |
| | M | 26.4 | 26.4 | WT | 0 | 26.4 | 4.4 | 30.6 | 8.1 | 87.4 |
| | F | 4.4 | 26.4 | 4.2 | 0 | 0 | 0 | 220.1 | WT | 4.7 |
| | Y | 8.6 | 4.1 | 4.1 | 0 | 7 | 0 | WT | 70.4 | 0 |
| | W | 0 | 4.4 | 0 | 0 | 0 | 0 | 88.2 | 0 | 0 |

As presented in Tables 10 to 12, it was revealed that, in any of "T395Q", "T395H," and "T395N," the catalytic activity for the production of 1,3-butadiene tended to further improve by replacement of position 394 with a different amino acid. Particularly surprisingly, in "T395H," the catalytic activity for the production of 1,3-butadiene was improved by 500 times or more in the case of replacing position 394 with serine, leucine, or methionine and 1000 times or more in the case of replacing the position with histidine as compared with wild type FDC.

INDUSTRIAL APPLICABILITY

As described above, the present invention makes it possible to provide an enzyme allowing production of an unsaturated hydrocarbon compound such as 1,3-butadiene with high productivity, and a method for producing an unsaturated hydrocarbon compound using the enzyme. In addition, the present invention makes it possible to produce an unsaturated hydrocarbon compound not by chemical synthesis but by biosynthesis, so that the burden on the environment is small. Therefore, the present invention is extremely useful in the production of raw materials of various synthetic polymers including synthetic rubber such as butadiene.

[Sequence Listing Free Text]
SEQ ID NO: 1
<223> ferulic acid decarboxylase
SEQ ID NO: 3
<223> codon-optimized sequence for expression in E. coli
<223> ferulic acid decarboxylase
SEQ ID NO: 4
<223> ferulic acid decarboxylase
SEQ ID NO: 5
<223> flavin prenyltransferase

The invention claimed is:

1. A method for producing an unsaturated hydrocarbon compound represented by the following formula (2) or a geometric isomer thereof, comprising: decarboxylating an unsaturated hydrocarbon dicarboxylic acid compound represented by the following formula (1) or a geometric isomer thereof in the presence of a ferulic acid decarboxylase in which an amino acid at position 395 of an amino add sequence set forth in SEQ ID NO: 2 or corresponding to the position is glutamine, histidine, asparagine, leucine, isoleucine, methionine, lysine, serine, arginine, tyrosine, or phenylalanine

[Chem. 1]

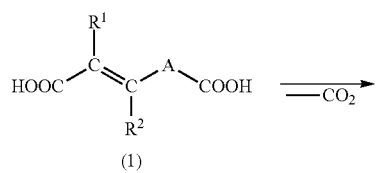

(1)

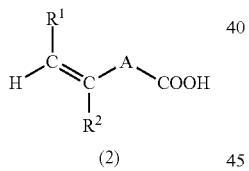

(2)

[In formulas (1) and (2), $R^1$ and $R^2$ each independently represent a hydrogen atom, a linear or branched alkyl group having 1 to 5 carbon atoms, a linear or branched alkoxy group having 1 to 5 carbon atoms, or hydroxyl group. "A" represents an optionally substituted linear hydrocarbon group having 0 to 5 carbon atoms, and may have a double bond formed between adjacent carbon atoms in the case of 2 to 5 carbon atoms.].

2. A method for producing an unsaturated hydrocarbon compound represented by the following formula (5) or a geometric isomer thereof, comprising: decarboxylating an unsaturated hydrocarbon dicarboxylic acid compound represented by the following formula (3) or a geometric isomer thereof in the presence of a ferulic acid decarboxylase in which an amino acid at position 395 of an amino acid sequence set forth in SEQ ID NO: 2 or corresponding to the position is glutamine, histidine, asparagine, leucine, isoleucine, methionine, lysine, serine, arginine, tyrosine, or phenylalanine

[Chem. 2]

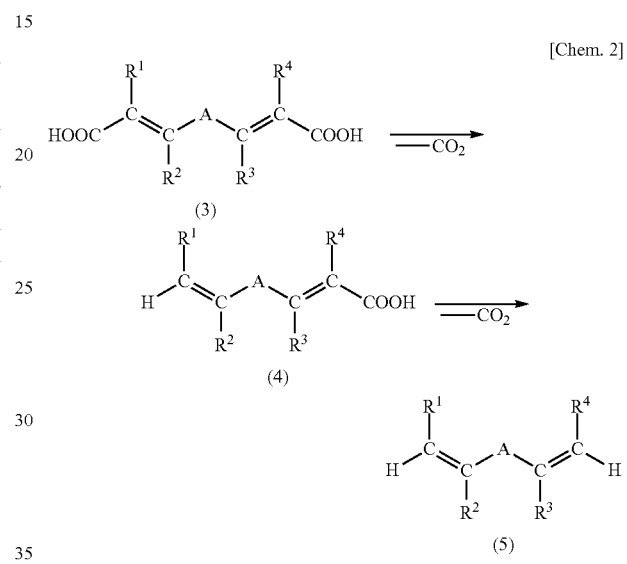

[In formulas (3) to (5), $R^1$, $R^2$, $R^3$, and $R^4$ each independently represent a hydrogen atom, a linear or branched alkyl group having 1 to 5 carbon atoms, a linear or branched alkoxy group having 1 to 5 carbon atoms, or hydroxyl group. "A" represents an optionally substituted linear hydrocarbon group having 0 to 5 carbon atoms, and may have a double bond formed between adjacent carbon atoms in the case of 2 to 5 carbon atoms.].

3. A method for producing an unsaturated hydrocarbon compound, comprising: culturing a host cell introduced with a DNA or a vector containing the DNA, the DNA encoding a ferulic acid decarboxylase in which an amino acid at position 395 of an amino acid sequence set forth in SEQ ID NO: 2 or corresponding to the position is glutamine, histidine, asparagine, leucine, isoleucine, methionine, lysine, serine, arginine, tyrosine, or phenylalanine; and collecting an unsaturated hydrocarbon compound represented by the following formula (2) or (5) or a geometric isomer thereof produced in the host cell and/or a cultured product thereof,

[Chem. 3]

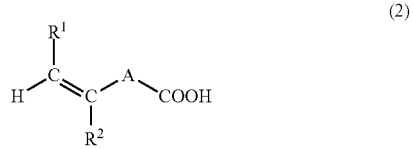

(2)

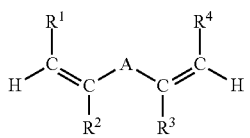
(5)

[In formulas (2) and (5), $R^1$, $R^2$, $R^3$, and $R^4$ each independently represent a hydrogen atom, a linear or branched alkyl group having 1 to 5 carbon atoms, a linear or branched alkoxy group having 1 to 5 carbon atoms, or hydroxyl group. "A" represents an optionally substituted linear hydrocarbon group having 0 to 5 carbon atoms, and may have a double bond formed between adjacent carbon atoms in the case of 2 to 5 carbon atoms.].

4. The method for producing an unsaturated hydrocarbon compound according to claim 1, wherein the ferulic acid decarboxylase is a ferulic acid decarboxylase in which the amino acid at position 395 of the amino acid sequence set forth in SEQ ID NO: 2 or corresponding to the position is glutamine, and an amino acid at position 394 of the amino acid sequence set forth in SEQ ID NO: 2 or corresponding to the position is histidine, methionine, serine, or leucine.

* * * * *

```
                      SEQUENCE LISTING

<160> NUMBER OF SEQ ID NOS: 6

<210> SEQ ID NO 1
<211> LENGTH: 1503
<212> TYPE: DNA
<213> ORGANISM: Aspergillus niger
<220> FEATURE:
<221> NAME/KEY: CDS
<222> LOCATION: (1)..(1503)
<223> OTHER INFORMATION: Ferulic acid decarboxylase

<400> SEQUENCE: 1 atg tct gcg caa cct gct cac ctg tgt ttc cgc tcc ttc gtc gaa gcc    48
Met Ser Ala Gln Pro Ala His Leu Cys Phe Arg Ser Phe Val Glu Ala
1               5                   10                  15 ctc aag gtc gac aac gac ctt gtt gaa atc aat acc cca att gac ccc    96
Leu Lys Val Asp Asn Asp Leu Val Glu Ile Asn Thr Pro Ile Asp Pro
                20                  25                  30 aat ctc gaa gct gct gct att acc cgc cga gta tgt gag acc aac gac   144
Asn Leu Glu Ala Ala Ala Ile Thr Arg Arg Val Cys Glu Thr Asn Asp
            35                  40                  45 aag gct cct tta ttc aac aac ctc atc ggc atg aaa aat ggc ctc ttc   192
Lys Ala Pro Leu Phe Asn Asn Leu Ile Gly Met Lys Asn Gly Leu Phe
        50                  55                  60 cgt ata ctt ggg gct cct ggc tct ctc agg aag tcg tct gct gat cgc   240
Arg Ile Leu Gly Ala Pro Gly Ser Leu Arg Lys Ser Ser Ala Asp Arg
65                  70                  75                  80
```

```
tac ggc cgc ctt gct cgt cac cta gcc ctc cca cct acg gcc tca atg         288
Tyr Gly Arg Leu Ala Arg His Leu Ala Leu Pro Pro Thr Ala Ser Met
                85              90              95 cgt gag att ctc gat aag atg ctc tcc gcc agc gat atg cct ccc atc         336
Arg Glu Ile Leu Asp Lys Met Leu Ser Ala Ser Asp Met Pro Pro Ile
            100             105             110 cct ccg acc att gtt ccc acc ggg cca tgc aag gag aac agc tta gat         384
Pro Pro Thr Ile Val Pro Thr Gly Pro Cys Lys Glu Asn Ser Leu Asp
            115             120             125 gac tct gaa ttc gac ctt acc gaa ctc ccc gtt cct ctt att cac aaa         432
Asp Ser Glu Phe Asp Leu Thr Glu Leu Pro Val Pro Leu Ile His Lys
        130             135             140 tcg gat ggt ggt aaa tac atc caa acc tat ggc atg cac att gtg cag         480
Ser Asp Gly Gly Lys Tyr Ile Gln Thr Tyr Gly Met His Ile Val Gln
145             150             155             160 tct ccg gat gga acc tgg acc aac tgg tct att gcc cgt gcg atg gtc         528
Ser Pro Asp Gly Thr Trp Thr Asn Trp Ser Ile Ala Arg Ala Met Val
                165             170             175 cat gac aag aac cat ctg acc ggc ctg gtt att ccc cct cag cac atc         576
His Asp Lys Asn His Leu Thr Gly Leu Val Ile Pro Pro Gln His Ile
            180             185             190 tgg cag att cac cag atg tgg aag aag gaa ggc cgc agt gac gtt ccc         624
Trp Gln Ile His Gln Met Trp Lys Lys Glu Gly Arg Ser Asp Val Pro
        195             200             205 tgg gct ttg gcc ttt ggt gtc cca ccc gct gcc att atg gcc tct agc         672
Trp Ala Leu Ala Phe Gly Val Pro Pro Ala Ala Ile Met Ala Ser Ser
        210             215             220 atg cct att ccc gat ggt gtc acc gaa gct ggg tac gtg gga gct atg         720
Met Pro Ile Pro Asp Gly Val Thr Glu Ala Gly Tyr Val Gly Ala Met
225             230             235             240 acg gga tcc tcc ctg gag ctt gtt aaa tgt gat acg aac gat cta tat         768
Thr Gly Ser Ser Leu Glu Leu Val Lys Cys Asp Thr Asn Asp Leu Tyr
                245             250             255 gtc ccc gct acc tca gaa atc gtt ctc gag ggc aca ctc tct atc agc         816
Val Pro Ala Thr Ser Glu Ile Val Leu Glu Gly Thr Leu Ser Ile Ser
            260             265             270 gag aca ggc cca gag gga cct ttc ggt gag atg cat ggt tac atc ttc         864
Glu Thr Gly Pro Glu Gly Pro Phe Gly Glu Met His Gly Tyr Ile Phe
        275             280             285 ccc ggg gat act cac ctc ggc gcc aaa tac aag gtt aac cgg atc acc         912
Pro Gly Asp Thr His Leu Gly Ala Lys Tyr Lys Val Asn Arg Ile Thr
        290             295             300 tac cgc aac aac gcc atc atg ccc atg tct tct tgt ggc cgc ttg acg         960
Tyr Arg Asn Asn Ala Ile Met Pro Met Ser Ser Cys Gly Arg Leu Thr
305             310             315             320 gat gaa acg cac acc atg atc ggc tct ctg gct gcg gcg gag atc cgt        1008
Asp Glu Thr His Thr Met Ile Gly Ser Leu Ala Ala Ala Glu Ile Arg
                325             330             335 aag ctc tgc cag cag aat gac ctc cct atc act gat gcc ttc gct cct        1056
Lys Leu Cys Gln Gln Asn Asp Leu Pro Ile Thr Asp Ala Phe Ala Pro
            340             345             350 ttc gag tct caa gtt acc tgg gtt gct ctg cgg gtc gat act gag aag        1104
Phe Glu Ser Gln Val Thr Trp Val Ala Leu Arg Val Asp Thr Glu Lys
        355             360             365 cta cgt gcc atg aag aca acg tct gag gga ttc cgc aag aga gtg gga        1152
Leu Arg Ala Met Lys Thr Thr Ser Glu Gly Phe Arg Lys Arg Val Gly
        370             375             380 gac gtc gtc ttc aac cac aag gcc gga tac acc att cat cgt ctg gtg        1200
Asp Val Val Phe Asn His Lys Ala Gly Tyr Thr Ile His Arg Leu Val
```

-continued

```
                385                 390                 395                 400
ttg gtc ggt gac gac att gat gtc tat gaa gga aag gat gtg ctc tgg          1248
Leu Val Gly Asp Asp Ile Asp Val Tyr Glu Gly Lys Asp Val Leu Trp
            405                 410                 415 gcg ttc tcc acc cgt tgc cgt cct ggt atg gac gag act ttg ttt gag          1296
Ala Phe Ser Thr Arg Cys Arg Pro Gly Met Asp Glu Thr Leu Phe Glu
        420                 425                 430 gat gtt cgt ggg ttc ccc ttg att ccg tat atg gga cac ggg aat ggg          1344
Asp Val Arg Gly Phe Pro Leu Ile Pro Tyr Met Gly His Gly Asn Gly
    435                 440                 445 ccc gcc cac cgc ggc gga aag gtt gtg tcc gac gct ctt atg ccg act          1392
Pro Ala His Arg Gly Gly Lys Val Val Ser Asp Ala Leu Met Pro Thr
450                 455                 460 gag tac acc act ggt cgc aac tgg gag gct gct gac ttc aac caa tct          1440
Glu Tyr Thr Thr Gly Arg Asn Trp Glu Ala Ala Asp Phe Asn Gln Ser
465                 470                 475                 480 tat ccc gag gat ctg aag cag aag gtt ttg gac aac tgg acg aag atg          1488
Tyr Pro Glu Asp Leu Lys Gln Lys Val Leu Asp Asn Trp Thr Lys Met
            485                 490                 495 ggt ttc agc aac taa                                                      1503
Gly Phe Ser Asn
            500
```

<210> SEQ ID NO 2
<211> LENGTH: 500
<212> TYPE: PRT
<213> ORGANISM: Aspergillus niger

<400> SEQUENCE: 2

```
Met Ser Ala Gln Pro Ala His Leu Cys Phe Arg Ser Phe Val Glu Ala
1               5                   10                  15

Leu Lys Val Asp Asn Asp Leu Val Glu Ile Asn Thr Pro Ile Asp Pro
            20                  25                  30

Asn Leu Glu Ala Ala Ala Ile Thr Arg Arg Val Cys Glu Thr Asn Asp
        35                  40                  45

Lys Ala Pro Leu Phe Asn Asn Leu Ile Gly Met Lys Asn Gly Leu Phe
    50                  55                  60

Arg Ile Leu Gly Ala Pro Gly Ser Leu Arg Lys Ser Ser Ala Asp Arg
65                  70                  75                  80

Tyr Gly Arg Leu Ala Arg His Leu Ala Leu Pro Pro Thr Ala Ser Met
                85                  90                  95

Arg Glu Ile Leu Asp Lys Met Leu Ser Ala Ser Asp Met Pro Pro Ile
            100                 105                 110

Pro Pro Thr Ile Val Pro Thr Gly Pro Cys Lys Glu Asn Ser Leu Asp
        115                 120                 125

Asp Ser Glu Phe Asp Leu Thr Glu Leu Pro Val Pro Leu Ile His Lys
    130                 135                 140

Ser Asp Gly Gly Lys Tyr Ile Gln Thr Tyr Gly Met His Ile Val Gln
145                 150                 155                 160

Ser Pro Asp Gly Thr Trp Thr Asn Trp Ser Ile Ala Arg Ala Met Val
                165                 170                 175

His Asp Lys Asn His Leu Thr Gly Leu Val Ile Pro Pro Gln His Ile
            180                 185                 190

Trp Gln Ile His Gln Met Trp Lys Lys Glu Gly Arg Ser Asp Val Pro
        195                 200                 205

Trp Ala Leu Ala Phe Gly Val Pro Pro Ala Ala Ile Met Ala Ser Ser
    210                 215                 220
```

```
Met Pro Ile Pro Asp Gly Val Thr Glu Ala Gly Tyr Val Gly Ala Met
225                 230                 235                 240

Thr Gly Ser Ser Leu Glu Leu Val Lys Cys Asp Thr Asn Asp Leu Tyr
            245                 250                 255

Val Pro Ala Thr Ser Glu Ile Val Leu Glu Gly Thr Leu Ser Ile Ser
        260                 265                 270

Glu Thr Gly Pro Glu Gly Pro Phe Gly Glu Met His Gly Tyr Ile Phe
    275                 280                 285

Pro Gly Asp Thr His Leu Gly Ala Lys Tyr Lys Val Asn Arg Ile Thr
290                 295                 300

Tyr Arg Asn Asn Ala Ile Met Pro Met Ser Ser Cys Gly Arg Leu Thr
305                 310                 315                 320

Asp Glu Thr His Thr Met Ile Gly Ser Leu Ala Ala Ala Glu Ile Arg
            325                 330                 335

Lys Leu Cys Gln Gln Asn Asp Leu Pro Ile Thr Asp Ala Phe Ala Pro
        340                 345                 350

Phe Glu Ser Gln Val Thr Trp Val Ala Leu Arg Val Asp Thr Glu Lys
    355                 360                 365

Leu Arg Ala Met Lys Thr Thr Ser Glu Gly Phe Arg Lys Arg Val Gly
370                 375                 380

Asp Val Val Phe Asn His Lys Ala Gly Tyr Thr Ile His Arg Leu Val
385                 390                 395                 400

Leu Val Gly Asp Asp Ile Asp Val Tyr Glu Gly Lys Asp Val Leu Trp
            405                 410                 415

Ala Phe Ser Thr Arg Cys Arg Pro Gly Met Asp Glu Thr Leu Phe Glu
        420                 425                 430

Asp Val Arg Gly Phe Pro Leu Ile Pro Tyr Met Gly His Gly Asn Gly
    435                 440                 445

Pro Ala His Arg Gly Gly Lys Val Val Ser Asp Ala Leu Met Pro Thr
450                 455                 460

Glu Tyr Thr Thr Gly Arg Asn Trp Glu Ala Ala Asp Phe Asn Gln Ser
465                 470                 475                 480

Tyr Pro Glu Asp Leu Lys Gln Lys Val Leu Asp Asn Trp Thr Lys Met
            485                 490                 495

Gly Phe Ser Asn
            500

<210> SEQ ID NO 3
<211> LENGTH: 1500
<212> TYPE: DNA
<213> ORGANISM: Artificial Sequence
<220> FEATURE:
<223> OTHER INFORMATION: Synthetic sequence, codon-optimized for E.coli
      expression
<220> FEATURE:
<221> NAME/KEY: CDS
<222> LOCATION: (1)..(1500)
<223> OTHER INFORMATION: Ferulic acid decarboxylase

<400> SEQUENCE: 3 atg agc gca cag cct gca cat ctg tgt ttt cgt agc ttt gtt gaa gca     48
Met Ser Ala Gln Pro Ala His Leu Cys Phe Arg Ser Phe Val Glu Ala
1               5                   10                  15 ctg aaa gtg gat aat gat ctg gtg gaa att aac acc ccg att gat ccg     96
Leu Lys Val Asp Asn Asp Leu Val Glu Ile Asn Thr Pro Ile Asp Pro
            20                  25                  30 aat ctg gaa gca gca gca att acc cgt cgt gtt tgt gaa acc aat gat    144
```

```
                Asn Leu Glu Ala Ala Ala Ile Thr Arg Arg Val Cys Glu Thr Asn Asp
                         35                  40                  45 aaa gca ccg ctg ttt aat aac ctg atc ggt atg aaa aat ggc ctg ttt        192
Lys Ala Pro Leu Phe Asn Asn Leu Ile Gly Met Lys Asn Gly Leu Phe
 50                  55                  60 cgt att ctg ggt gca ccg ggt agc ctg cgt aaa agc agc gca gat cgt        240
Arg Ile Leu Gly Ala Pro Gly Ser Leu Arg Lys Ser Ser Ala Asp Arg
 65                  70                  75                  80 tat ggt cgt ctg gca cgt cat ctg gca ctg cct ccg acc gca agc atg        288
Tyr Gly Arg Leu Ala Arg His Leu Ala Leu Pro Pro Thr Ala Ser Met
                 85                  90                  95 cgt gaa att ctg gat aaa atg ctg agc gca agc gat atg cct ccg att        336
Arg Glu Ile Leu Asp Lys Met Leu Ser Ala Ser Asp Met Pro Pro Ile
                100                 105                 110 ccg cct acc att gtt ccg acc ggt ccg tgt aaa gaa aat agc ctg gat        384
Pro Pro Thr Ile Val Pro Thr Gly Pro Cys Lys Glu Asn Ser Leu Asp
            115                 120                 125 gat agc gaa ttt gat ctg acc gaa ctg ccg gtt ccg ctg att cat aaa        432
Asp Ser Glu Phe Asp Leu Thr Glu Leu Pro Val Pro Leu Ile His Lys
130                 135                 140 agt gat ggt ggc aaa tat atc cag acc tat ggt atg cat att gtg cag        480
Ser Asp Gly Gly Lys Tyr Ile Gln Thr Tyr Gly Met His Ile Val Gln
145                 150                 155                 160 agt ccg gat ggc acc tgg acc aat tgg agc att gca cgt gcc atg gtt        528
Ser Pro Asp Gly Thr Trp Thr Asn Trp Ser Ile Ala Arg Ala Met Val
                165                 170                 175 cat gat aaa aat cat ctg acc ggt ctg gtt att ccg cct cag cat att        576
His Asp Lys Asn His Leu Thr Gly Leu Val Ile Pro Pro Gln His Ile
            180                 185                 190 tgg cag att cat cag atg tgg aaa aaa gaa ggt cgt agc gac gtt ccg        624
Trp Gln Ile His Gln Met Trp Lys Lys Glu Gly Arg Ser Asp Val Pro
        195                 200                 205 tgg gca ctg gca ttt ggt gtt cct ccg gca gcc att atg gca agc agc        672
Trp Ala Leu Ala Phe Gly Val Pro Pro Ala Ala Ile Met Ala Ser Ser
    210                 215                 220 atg ccg att ccg gat ggt gtt acc gaa gca ggt tat gtt ggt gca atg        720
Met Pro Ile Pro Asp Gly Val Thr Glu Ala Gly Tyr Val Gly Ala Met
225                 230                 235                 240 acc ggt agc agc ctg gaa ctg gtt aaa tgc gat acc aat gat ctg tat        768
Thr Gly Ser Ser Leu Glu Leu Val Lys Cys Asp Thr Asn Asp Leu Tyr
                245                 250                 255 gtt ccg gca acc agc gaa att gtt ctg gaa ggc acc ctg agc att agc        816
Val Pro Ala Thr Ser Glu Ile Val Leu Glu Gly Thr Leu Ser Ile Ser
            260                 265                 270 gaa acc ggt ccg gaa ggt ccg ttt ggt gaa atg cat ggt tat atc ttt        864
Glu Thr Gly Pro Glu Gly Pro Phe Gly Glu Met His Gly Tyr Ile Phe
        275                 280                 285 ccg ggt gat acc cat ctg ggt gcc aaa tac aaa gtt aat cgt att acc        912
Pro Gly Asp Thr His Leu Gly Ala Lys Tyr Lys Val Asn Arg Ile Thr
    290                 295                 300 tat cgc aac aac gcc att atg ccg atg agc agc tgc ggt cgt ctg acc        960
Tyr Arg Asn Asn Ala Ile Met Pro Met Ser Ser Cys Gly Arg Leu Thr
305                 310                 315                 320 gat gaa acc cat acc atg att ggt agc ctg gca gca gcc gaa att cgt       1008
Asp Glu Thr His Thr Met Ile Gly Ser Leu Ala Ala Ala Glu Ile Arg
                325                 330                 335 aaa ctg tgt cag cag aat gat ctg ccg att acc gat gca ttt gca ccg       1056
Lys Leu Cys Gln Gln Asn Asp Leu Pro Ile Thr Asp Ala Phe Ala Pro
            340                 345                 350
```

-continued

| | |
|---|---|
| ttt gaa agc cag gtt acc tgg gtt gca ctg cgt gtt gat acc gaa aaa<br>Phe Glu Ser Gln Val Thr Trp Val Ala Leu Arg Val Asp Thr Glu Lys<br>         355                      360                    365 | 1104 |
| ctg cgt gca atg aaa acc acc agt gaa ggt ttt cgt aaa cgc gtt ggt<br>Leu Arg Ala Met Lys Thr Thr Ser Glu Gly Phe Arg Lys Arg Val Gly<br>370                      375                      380 | 1152 |
| gat gtg gtg ttt aat cat aaa gcc ggt tat acc att cat cgt ctg gtt<br>Asp Val Val Phe Asn His Lys Ala Gly Tyr Thr Ile His Arg Leu Val<br>385                      390                      395                      400 | 1200 |
| ctg gtg ggt gat gat att gat gtt tat gaa ggt aaa gat gtg ctg tgg<br>Leu Val Gly Asp Asp Ile Asp Val Tyr Glu Gly Lys Asp Val Leu Trp<br>                      405                      410                      415 | 1248 |
| gca ttt agc acc cgt tgt cgt ccg ggt atg gat gaa aca ctg ttt gaa<br>Ala Phe Ser Thr Arg Cys Arg Pro Gly Met Asp Glu Thr Leu Phe Glu<br>                      420                      425                      430 | 1296 |
| gat gtt cgt ggt ttt cct ctg att ccg tat atg ggt cat ggt aat ggt<br>Asp Val Arg Gly Phe Pro Leu Ile Pro Tyr Met Gly His Gly Asn Gly<br>                      435                      440                      445 | 1344 |
| ccg gca cat cgt ggt ggt aaa gtt gtt agt gat gca ctg atg ccg acc<br>Pro Ala His Arg Gly Gly Lys Val Val Ser Asp Ala Leu Met Pro Thr<br>450                      455                      460 | 1392 |
| gaa tat acc acc ggt cgt aat tgg gaa gca gcc gat ttt aat cag agc<br>Glu Tyr Thr Thr Gly Arg Asn Trp Glu Ala Ala Asp Phe Asn Gln Ser<br>465                      470                      475                      480 | 1440 |
| tat ccg gaa gat ctg aaa cag aaa gtg ctg gat aat tgg acc aaa atg<br>Tyr Pro Glu Asp Leu Lys Gln Lys Val Leu Asp Asn Trp Thr Lys Met<br>                      485                      490                      495 | 1488 |
| ggt ttt agc aat<br>Gly Phe Ser Asn<br>                500 | 1500 |

<210> SEQ ID NO 4
<211> LENGTH: 500
<212> TYPE: PRT
<213> ORGANISM: Artificial Sequence
<220> FEATURE:
<223> OTHER INFORMATION: Synthetic Construct

<400> SEQUENCE: 4

Met Ser Ala Gln Pro Ala His Leu Cys Phe Arg Ser Phe Val Glu Ala
1               5                   10                  15

Leu Lys Val Asp Asn Asp Leu Val Glu Ile Asn Thr Pro Ile Asp Pro
            20                  25                  30

Asn Leu Glu Ala Ala Ala Ile Thr Arg Arg Val Cys Glu Thr Asn Asp
        35                  40                  45

Lys Ala Pro Leu Phe Asn Asn Leu Ile Gly Met Lys Asn Gly Leu Phe
    50                  55                  60

Arg Ile Leu Gly Ala Pro Gly Ser Leu Arg Lys Ser Ser Ala Asp Arg
65                  70                  75                  80

Tyr Gly Arg Leu Ala Arg His Leu Ala Leu Pro Pro Thr Ala Ser Met
                85                  90                  95

Arg Glu Ile Leu Asp Lys Met Leu Ser Ala Ser Asp Met Pro Pro Ile
            100                 105                 110

Pro Pro Thr Ile Val Pro Thr Gly Pro Cys Lys Glu Asn Ser Leu Asp
        115                 120                 125

Asp Ser Glu Phe Asp Leu Thr Glu Leu Pro Val Pro Leu Ile His Lys
    130                 135                 140

Ser Asp Gly Gly Lys Tyr Ile Gln Thr Tyr Gly Met His Ile Val Gln
145                 150                 155                 160

```
Ser Pro Asp Gly Thr Trp Thr Asn Trp Ser Ile Ala Arg Ala Met Val
            165                 170                 175

His Asp Lys Asn His Leu Thr Gly Leu Val Ile Pro Pro Gln His Ile
        180                 185                 190

Trp Gln Ile His Gln Met Trp Lys Lys Glu Gly Arg Ser Asp Val Pro
    195                 200                 205

Trp Ala Leu Ala Phe Gly Val Pro Ala Ala Ile Met Ala Ser Ser
210                 215                 220

Met Pro Ile Pro Asp Gly Val Thr Glu Ala Gly Tyr Val Gly Ala Met
225                 230                 235                 240

Thr Gly Ser Ser Leu Glu Leu Val Lys Cys Asp Thr Asn Asp Leu Tyr
            245                 250                 255

Val Pro Ala Thr Ser Glu Ile Val Leu Glu Gly Thr Leu Ser Ile Ser
        260                 265                 270

Glu Thr Gly Pro Glu Gly Pro Phe Gly Glu Met His Gly Tyr Ile Phe
    275                 280                 285

Pro Gly Asp Thr His Leu Gly Ala Lys Tyr Lys Val Asn Arg Ile Thr
290                 295                 300

Tyr Arg Asn Asn Ala Ile Met Pro Met Ser Ser Cys Gly Arg Leu Thr
305                 310                 315                 320

Asp Glu Thr His Thr Met Ile Gly Ser Leu Ala Ala Glu Ile Arg
            325                 330                 335

Lys Leu Cys Gln Gln Asn Asp Leu Pro Ile Thr Asp Ala Phe Ala Pro
        340                 345                 350

Phe Glu Ser Gln Val Thr Trp Val Ala Leu Arg Val Asp Thr Glu Lys
    355                 360                 365

Leu Arg Ala Met Lys Thr Thr Ser Glu Gly Phe Arg Lys Arg Val Gly
370                 375                 380

Asp Val Val Phe Asn His Lys Ala Gly Tyr Thr Ile His Arg Leu Val
385                 390                 395                 400

Leu Val Gly Asp Asp Ile Asp Val Tyr Glu Gly Lys Asp Val Leu Trp
            405                 410                 415

Ala Phe Ser Thr Arg Cys Arg Pro Gly Met Asp Glu Thr Leu Phe Glu
        420                 425                 430

Asp Val Arg Gly Phe Pro Leu Ile Pro Tyr Met Gly His Gly Asn Gly
    435                 440                 445

Pro Ala His Arg Gly Gly Lys Val Val Ser Asp Ala Leu Met Pro Thr
450                 455                 460

Glu Tyr Thr Thr Gly Arg Asn Trp Glu Ala Ala Asp Phe Asn Gln Ser
465                 470                 475                 480

Tyr Pro Glu Asp Leu Lys Gln Lys Val Leu Asp Asn Trp Thr Lys Met
            485                 490                 495

Gly Phe Ser Asn
            500
```

<210> SEQ ID NO 5  
<211> LENGTH: 570  
<212> TYPE: DNA  
<213> ORGANISM: Escherichia coli  
<220> FEATURE:  
<221> NAME/KEY: CDS  
<222> LOCATION: (1)..(570)  
<223> OTHER INFORMATION: Flavin prenyltransferase

<400> SEQUENCE: 5

```
atg aaa cga ctc att gta ggc atc agc ggt gcc agc ggc gcg att tat      48
Met Lys Arg Leu Ile Val Gly Ile Ser Gly Ala Ser Gly Ala Ile Tyr
1               5                   10                  15 ggc gtg cgc tta tta cag gtt ctg cgc gat gtc aca gat atc gaa acg      96
Gly Val Arg Leu Leu Gln Val Leu Arg Asp Val Thr Asp Ile Glu Thr
                20                  25                  30 cat ctg gtg atg agc cag gca gcg cgc cag acc tta tcc ctc gaa acg     144
His Leu Val Met Ser Gln Ala Ala Arg Gln Thr Leu Ser Leu Glu Thr
            35                  40                  45 gat ttt tct ctg cgc gaa gtg cag gca tta gcc gat gtc acg cac gat     192
Asp Phe Ser Leu Arg Glu Val Gln Ala Leu Ala Asp Val Thr His Asp
        50                  55                  60 gcg cgc gat att gcc gcc agc atc tct tcc ggt tct ttc cag acg ctg     240
Ala Arg Asp Ile Ala Ala Ser Ile Ser Ser Gly Ser Phe Gln Thr Leu
65                  70                  75                  80 ggg atg gtg att tta ccc tgt tca atc aaa acc ctt tcc ggc att gtc     288
Gly Met Val Ile Leu Pro Cys Ser Ile Lys Thr Leu Ser Gly Ile Val
                85                  90                  95 cat agc tat act gat ggc tta ctg acc cgt gcg gca gat gtg gtg ctg     336
His Ser Tyr Thr Asp Gly Leu Leu Thr Arg Ala Ala Asp Val Val Leu
                100                 105                 110 aaa gag cgt cgc ccg ttg gtg ctc tgc gtg cgt gaa aca cca ttg cac     384
Lys Glu Arg Arg Pro Leu Val Leu Cys Val Arg Glu Thr Pro Leu His
            115                 120                 125 tta ggc cat ctg cgt tta atg act cag gcg gca gaa atc ggt gcg gtg     432
Leu Gly His Leu Arg Leu Met Thr Gln Ala Ala Glu Ile Gly Ala Val
        130                 135                 140 att atg cct ccc gtt ccg gcg ttt tat cat cgc ccg caa tcc ctt gat     480
Ile Met Pro Pro Val Pro Ala Phe Tyr His Arg Pro Gln Ser Leu Asp
145                 150                 155                 160 gat gtg ata aat cag acg gtt aat cgt gtt ctt gac cag ttt gcg ata     528
Asp Val Ile Asn Gln Thr Val Asn Arg Val Leu Asp Gln Phe Ala Ile
                165                 170                 175 acc ctt cct gaa gat ctc ttt gcc cgc tgg cag ggc gca taa             570
Thr Leu Pro Glu Asp Leu Phe Ala Arg Trp Gln Gly Ala
                180                 185

<210> SEQ ID NO 6
<211> LENGTH: 189
<212> TYPE: PRT
<213> ORGANISM: Escherichia coli

<400> SEQUENCE: 6

Met Lys Arg Leu Ile Val Gly Ile Ser Gly Ala Ser Gly Ala Ile Tyr
1               5                   10                  15

Gly Val Arg Leu Leu Gln Val Leu Arg Asp Val Thr Asp Ile Glu Thr
                20                  25                  30

His Leu Val Met Ser Gln Ala Ala Arg Gln Thr Leu Ser Leu Glu Thr
            35                  40                  45

Asp Phe Ser Leu Arg Glu Val Gln Ala Leu Ala Asp Val Thr His Asp
        50                  55                  60

Ala Arg Asp Ile Ala Ala Ser Ile Ser Ser Gly Ser Phe Gln Thr Leu
65                  70                  75                  80

Gly Met Val Ile Leu Pro Cys Ser Ile Lys Thr Leu Ser Gly Ile Val
                85                  90                  95

His Ser Tyr Thr Asp Gly Leu Leu Thr Arg Ala Ala Asp Val Val Leu
                100                 105                 110

Lys Glu Arg Arg Pro Leu Val Leu Cys Val Arg Glu Thr Pro Leu His
            115                 120                 125
```

```
Leu Gly His Leu Arg Leu Met Thr Gln Ala Ala Glu Ile Gly Ala Val
    130                 135                 140

Ile Met Pro Pro Val Pro Ala Phe Tyr His Arg Pro Gln Ser Leu Asp
145                 150                 155                 160

Asp Val Ile Asn Gln Thr Val Asn Arg Val Leu Asp Gln Phe Ala Ile
            165                 170                 175

Thr Leu Pro Glu Asp Leu Phe Ala Arg Trp Gln Gly Ala
            180                 185
```